United States Patent [19]

Simmons et al.

[11] Patent Number: 5,747,662

[45] Date of Patent: May 5, 1998

[54] METHODS AND COMPOSITIONS FOR SECRETION OF HETEROLOGOUS POLYPEPTIDES

[75] Inventors: Laura C. Simmons, Burlingame; Daniel G. Yansura, Pacifica, both of Calif.

[73] Assignee: Genentech, Inc., S. San Francisco, Calif.

[21] Appl. No.: 398,617

[22] Filed: Mar. 1, 1995

[51] Int. Cl.$^6$ .................................................. C07H 21/04
[52] U.S. Cl. ........................................................ 536/24.1
[58] Field of Search .......................................... 536/24.1

[56] References Cited

U.S. PATENT DOCUMENTS

| | | | |
|---|---|---|---|
| 4,963,495 | 10/1990 | Chang et al. | 435/320.1 |
| 5,232,840 | 8/1993 | Olins | 435/69.1 |

FOREIGN PATENT DOCUMENTS

| | | |
|---|---|---|
| 0177343-A1 | 4/1986 | European Pat. Off. |
| 95/25743 | 9/1995 | WIPO |

OTHER PUBLICATIONS

Greenberg et al., "High-Level Expression and Secretion of a Lysine-Containing Analog of Escherichia coli Heat-Stable Enterotoxin" *Protein Expression Purification* 2(5-6):394-401 (Oct.-Dec. 1991).

Ibrahimi et al., "A functional interaction between the signal peptide and the translation apparatus is detected by the use of a single point mutation which blocks translation apprararatus is dected by . . . " *Journal of Biological Chemistry* 262(21):10189-10194 (Jul. 25, 1987).

Chang et al., "High-level secretion of human growth hormone by Escherichia coli" *Gene* 55:189-196 (1987).

Denefle et al., "Heterologous protein export in Escherichia coli: influence of bacterial signal peptides on the export of human interleukin 1β" *Gene* 85:499-510 (1989).

Fujimoto et al., "Expression and secretion of human epidermal growth factor by Escherichia coli using enterotoxin signal sequences" *J. Biotech.* 8:77-86 (1988).

Goldstein et al., "Enhancement of Protein Translocation across the Membrane by Specific Mutations in the Hydrophobic Region of the Signal Peptide" *J. Bact.* 172(3):1225-1231 (Mar. 1990).

Gray et al., "Periplasmic production of correctly processed human growth hormone in Escherichia coli: natural and bacterial signal sequences are interchangeable" *Gene* 39:247-254 (1985).

Klein et al., "Effects of signal peptide changes on the secretion of bovine somatotropin (bST) from Escherichia coli" *Protein Engineering* 5(6):511-517 (1992).

Lehnhardt et al., "The Differential Effect on Two Hybrid Proteins of Deletion Mutations within the Hydrophobic Region of the Escherichia coli OmpA Signal Peptide" *Journal of Biological Chemistry* 262(4):1716-1719 (Feb. 5, 1987).

Matteucci et al., "Alkaline Phosphatase Fusions: A Tag to Identify Mutations that Result in Increased Expression of Secreted Human Growth Hormone from E. Coli" *Biotechnology* 4:51-55 (Jan. 1986).

Morioka-Fujimoto et al., "Modified Enterotoxin Signal Sequences Increase Secretion Level of the Recombinant Human Epidermal Growth Factor in Escherichia coli" *Journal of Biological Chemistry* 266(3):1728-1732 (1991).

Perez-Perez et al., "Increasing the Efficiency of Protein Export in Escherichia coli" *Bio/Technology* 12:178-180 (Feb. 12, 1994).

van Dijl et al., "Signal peptidase I overproduction results in increased efficiencies of export and maturation of hybrid secretory proteins in Escherichia coli" *Mol. Gen. Genet.* 227:40-48 (1991).

Watson, Marion E.E., "Compilation of published signal sequences" *Nucl. Acids. Res.* 12(13):5145-5164 (1984).

Wong et al., "Expression of secreted insulin-like growth factor-1 in Escherichia coli" *Gene* 68:193-203 (1988).

*Primary Examiner*—James Ketter
*Assistant Examiner*—John S. Brusca
*Attorney, Agent, or Firm*—Walter H. Dreger

[57] ABSTRACT

The instant invention discloses the unexpected result that mutant signal sequences with reduced translational strength provided essentially complete processing and high levels of expression of a polypeptide of interest as compared to wild type signal sequences, and that many mammalian polypeptides require a narrow range of translation levels to achieve maximum secretion. A set of signal sequence vectors provides a range of translational strengths for optimizing expression of a polypeptide of interest.

11 Claims, 21 Drawing Sheets

```
       ecoRI
  1  GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
     CTTAAGTTGA AGAGGTATGA AACCTATTCC TTTATGTCTG TACTTTTTAG AGTAACGACT CAACAATAAA TTCGAACGGG CTTTTCTTCT TCTCAGCTTA 101  GAACTGTGTG CGCAGGTAGA AGCTTTGGAG ATTATCGTCA CTGCAATGCT TCGCAATATG GCGCAAAATG ACCAACAGCG GTTGATTGAT CAGTAGAGG
     CTTGACACAC GCGTCCATCT TCGAAACCTC TAATAGCAGT GACGTTACGA AGCGTTATAC CGCGTTTTAC TGGTTGTCGC CAACTAACTA GTCCATCTCC 201  GGGCGCTGTA CGAGGTAAAG CCCGATGCCA GCATTCCTGA CGACGATACG GAGCTGCTGC GCGATTACGT AAAGAAGTTA TTGAAGCATC CTCGTCAGTA
     CCCGCGACAT GCTCCATTTC GGGCTACGGT CGTAAGGACT GCTGCTATGC CTCGACGACG CGCTAATGCA TTTCTTCAAT AACTTCGTAG GAGCAGTCAT 301  AAAAGTTAAT CTTTTCAACA GCTGTCATAA AGTTGTCACG GCCGAGACTT ATAGTCGCTT TGTTTTTATT TTTTAATGTA TTTGTAACTA GTACGCAAGT
     TTTTCAATTA GAAAAGTTGT CGACAGTGCT CGGCTCTGAA TATCAGCGAA ACAAAAATAA AAAATTACAT AAACATTGAT CATGCGTTCA Trp SD   xbaI             STII SD
401  TCACGTAAAA AGGTATCTA GAGGTTGAGG TGATTTT     ATG AAA AAG AAT ATC GCA TTT CTT CTT GCA TCT ATG TTC GTT TTT TCT
     AGTGCATTTT TCCCATAGAT CTCCAACTCC ACTAAAA    TAC TTT TTC TTA TAG CGT AAA GAA GAA CGT AGA TAC AAG CAA AAA AGA
                                                Met Lys Lys Asn Ile Ala Phe Leu Leu Ala Ser Met Phe Val Phe Ser
                                                 1

486  ATT GCT ACA AAT GCC TAT GCA   (SEQ ID NO: 13)
     TAA CGA TGT TTA CGG ATA CGT   (SEQ ID NO: 14)
 17  Ile Ala Thr Asn Ala Tyr Ala
```

```
pPho31 (Wild type STII + MluI site)
       TCTAGAGGTTGAGGTGATTTT ATG AAA AAG AAT ATC GCA TTT CTT CTT GCA TCT ATG TTC GTT pPho21 (STIIC)
       TCTAGAATT ATG AAA AAG AAT ATC GCA TTT CTT CTT GCA TCT ATG TTC GTT pPho41 (STIIBK#131)
       TCTAGAATT ATG AAG AAG AAT ATT GCG TTC CTA CTT GCC TCT ATG TTT GTC pPho51 (STIILys - unless otherwise noted this
sequence is the TIR=1 used in the examples)
       TCTAGAATT ATG AAG AAT ATC GCA TTT CTT CTT GCA TCT ATG TTC GTT pSTBKPhoA#116
       TCTAGAATT ATG AAA AAA AAC ATC GCA TTT CTT CTT GCA TCT ATG TTC GTT pSTBKPhoA#81
       TCTAGAATT ATG AAA AAA AAC ATT GCC TTT CTT CTT GCA TCT ATG TTC GTT pSTBKPhoA#107
       TCTAGAATT ATG AAG AAA AAC ATC GCT TTT CTT CTT GCA TCT ATG TTC GTT pSTBKPhoA#86
       TCTAGAATT ATG AAA AAG AAC ATA GCG TTT CTT CTT GCA TCT ATG TTC GTT pST116Pho
       TCTAGAGGTTGAGGTGATTTT ATG AAA AAA AAC ATC GCA TTT CTT CTT GCA TCT ATG TTC GTT
```

| Sequence | | TIR RELATIVE STRENGTH |
|---|---|---|
| TTT TCT ATT GCT ACA AAY GCS TAT GCM* | (SEQ ID NO:15) | 9 |
| TTT TCT ATT GCT ACA AAC GCG TAT GCM | (SEQ ID NO:16) | 7 |
| TTT TCT ATA GCT ACA AAC GCG TAT GCM | (SEQ ID NO:17) | 3 |
| TTT TCT ATT GCT ACA AAC GCG TAT GCM | (SEQ ID NO:18) | 1 |
| TTT TCT ATT GCT ACA AAC GCG TAT GCM | (SEQ ID NO:19) | 9 |
| TTT TCT ATT GCT ACA AAC GCG TAT GCM | (SEQ ID NO:20) | 4 |
| TTT TCT ATT GCT ACA AAC GCG TAT GCM | (SEQ ID NO:21) | 2 |
| TTT TCT ATT GCT ACA AAC GCG TAT GCM | (SEQ ID NO:22) | 1 |
| TTT TCT ATT GCT ACA AAC GCG TAT GCM | (SEQ ID NO:23) | 13 |

FIG. 14B

* The codons for the last four amino acids of this sequence may differ in some of the examples of protein secretion. For example, in the IGF-1, VEGF165 and RANTES secretion plasmids, the sequence is AAT GCC TAT GCA; may vary in The last codon for the last amino acid in every sequence listed may vary in the examples of protein secretion - GCC and GCA were both used.

* One of the nucleotide sequences listed in Figure 14
(STII Shine-Dalgarno may also be included).

* One of the nucleotide sequences listed in Figure 14
(STII Shine-Dalgarno may also be included).

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 88 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GCATGTCTAG AATTATGAAR AARAAYATHG CNTTYCTNCT NGCNTCNATG           50

TTYGTNTTYT CNATHGCTAC AAACGCGTAT GCCACTCT                        88
```

( 2 ) INFORMATION FOR SEQ ID NO:2:

( i ) SEQUENCE CHARACTERISTICS:

(A) LENGTH: 36 bases
(B) TYPE: nucleic acid
(C) STRANDEDNESS: single
(D) TOPOLOGY: linear (xi) SEQUENCE DESCRIPTION: SEQ ID NO:2:

TTCAGCACCG CACAGAGTGG CATACGCGTT TGTAGC 36

(2) INFORMATION FOR SEQ ID NO:3:

(i) SEQUENCE CHARACTERISTICS:
(A) LENGTH: 82 bases
(B) TYPE: nucleic acid
(C) STRANDEDNESS: single
(D) TOPOLOGY: linear (xi) SEQUENCE DESCRIPTION: SEQ ID NO:3:

CTAGAATTAT GAAAAAGAAT ATCGCATTTC TTCTTGCATC TATGTTCGTT 50

TTTTCTATTG CTACAAACGC GTATGCCACT CT 82

(2) INFORMATION FOR SEQ ID NO:4:

(i) SEQUENCE CHARACTERISTICS:
(A) LENGTH: 75 bases
(B) TYPE: nucleic acid
(C) STRANDEDNESS: single
(D) TOPOLOGY: linear (xi) SEQUENCE DESCRIPTION: SEQ ID NO:4:

GTGGCATACG CGTTTGTAGC AATAGAAAAA ACGAACATAG ATGCAAGAAG 50

AAATGCGATA TTCTTTTTCA TAATT 75

(2) INFORMATION FOR SEQ ID NO:5:

(i) SEQUENCE CHARACTERISTICS:
(A) LENGTH: 67 bases
(B) TYPE: nucleic acid
(C) STRANDEDNESS: single
(D) TOPOLOGY: linear (xi) SEQUENCE DESCRIPTION: SEQ ID NO:5:

CTAGAATTAT GAAGAAGAAT ATCGCATTTC TTCTTGCATC TATGTTCGTT 50

TTTTCTATTG CTACAAA 67

(2) INFORMATION FOR SEQ ID NO:6:

(i) SEQUENCE CHARACTERISTICS:
(A) LENGTH: 67 bases
(B) TYPE: nucleic acid
(C) STRANDEDNESS: single
(D) TOPOLOGY: linear (xi) SEQUENCE DESCRIPTION: SEQ ID NO:6:

CGCGTTTGTA GCAATAGAAA AACGAACAT AGATGCAAGA AGAAATGCGA 50

TATTCTTCTT CATAATT 67

(2) INFORMATION FOR SEQ ID NO:7:

(i) SEQUENCE CHARACTERISTICS:
(A) LENGTH: 79 bases
(B) TYPE: nucleic acid
(C) STRANDEDNESS: single
(D) TOPOLOGY: linear (xi) SEQUENCE DESCRIPTION: SEQ ID NO:7:

```
CGCGTATGCC CGGACACCAG AAATGCCTGT TCTGGAAAAC CGGGCTGCTC         50

AGGGCGATAT TACTGCACCC GGCGGTGCT                              79
```

( 2 ) INFORMATION FOR SEQ ID NO:8:

( i ) SEQUENCE CHARACTERISTICS:
        ( A ) LENGTH: 71 bases
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
CCGCCGGGTG CAGTAATATC GCCCTGAGCA GCCCGGTTTT CCAGAACAGG         50

CATTTCTGGT GTCCGGGCAT A                                       71
```

( 2 ) INFORMATION FOR SEQ ID NO:9:

( i ) SEQUENCE CHARACTERISTICS:
        ( A ) LENGTH: 83 bases
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
GCATGTCTAG AATTATGAAR AARAAYATHG CNTTTCTTCT TGCATCTATG         50

TTCGTTTTTT CTATTGCTAC AAACGCGTAT GCC                          83
```

( 2 ) INFORMATION FOR SEQ ID NO:10:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
AGTGGCATAC GCGTTTGTAG CAATAGA                                 27
```

( 2 ) INFORMATION FOR SEQ ID NO:11:

( i ) SEQUENCE CHARACTERISTICS:
        ( A ) LENGTH: 79 bases
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
CTAGAGGTTG AGGTGATTTT ATGAAAAAAA ACATCGCATT TCTTCTTGCA         50

TCTATGTTCG TTTTTCTAT TGCTACAAA                                79
```

( 2 ) INFORMATION FOR SEQ ID NO:12:

( i ) SEQUENCE CHARACTERISTICS:
        ( A ) LENGTH: 79 bases
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
CGCGTTTGTA GCAATAGAAA AAACGAACAT AGATGCAAGA AGAAATGCGA         50

TGTTTTTTTT CATAAAATCA CCTCAACCT                               79
```

( 2 ) INFORMATION FOR SEQ ID NO:13:

-continued ( i ) SEQUENCE CHARACTERISTICS:
    ( A ) LENGTH: 506 bases
    ( B ) TYPE: nucleic acid
    ( C ) STRANDEDNESS: double
    ( D ) TOPOLOGY: linear ( x i ) SEQUENCE DESCRIPTION: SEQ ID NO:13:

```
GAATTCAACT  TCTCCATACT  TTGGATAAGG  AAATACAGAC  ATGAAAAATC           50
TCATTGCTGA  GTTGTTATTT  AAGCTTGCCC  AAAAAGAAGA  AGAGTCGAAT          100
GAACTGTGTG  CGCAGGTAGA  AGCTTGGAG   ATTATCGTCA  CTGCAATGCT          150
TCGCAATATG  GCGCAAAATG  ACCAACAGCG  GTTGATTGAT  CAGGTAGAGG          200
GGGCGCTGTA  CGAGGTAAAG  CCCGATGCCA  GCATTCCTGA  CGACGATACG          250
GAGCTGCTGC  GCGATTACGT  AAAGAAGTTA  TTGAAGCATC  CTCGTCAGTA          300
AAAAGTTAAT  CTTTTCAACA  GCTGTCATAA  AGTTGTCACG  GCCGAGACTT          350
ATAGTCGCTT  TGTTTTTATT  TTTTAATGTA  TTTGTAACTA  GTACGCAAGT          400
TCACGTAAAA  AGGGTATCTA  GAGGTTGAGG  TGATTTTATG  AAAAAGAATA          450
TCGCATTTCT  TCTTGCATCT  ATGTTCGTTT  TTCTATTGC   TACAAATGCC          500
TATGCA                                                              506
```

( 2 ) INFORMATION FOR SEQ ID NO:14:

( i ) SEQUENCE CHARACTERISTICS:
        ( A ) LENGTH: 23 amino acids
        ( B ) TYPE: amino acid
        ( D ) TOPOLOGY: linear ( x i ) SEQUENCE DESCRIPTION: SEQ ID NO:14:

```
Met  Lys  Lys  Asn  Ile  Ala  Phe  Leu  Leu  Ala  Ser  Met  Phe  Val  Phe
 1              5                        10                          15
Ser  Ile  Ala  Thr  Asn  Ala  Tyr  Ala
                20             23
```

( 2 ) INFORMATION FOR SEQ ID NO:15:

( i ) SEQUENCE CHARACTERISTICS:
        ( A ) LENGTH: 90 bases
        ( B ) TYPE: nucleic acid
        ( C ) STRANDEDNESS: double
        ( D ) TOPOLOGY: linear ( x i ) SEQUENCE DESCRIPTION: SEQ ID NO:15:

```
TCTAGAGGTT  GAGGTGATTT  TATGAAAAAG  AATATCGCAT  TTCTTCTTGC           50
ATCTATGTTC  GTTTTTTCTA  TTGCTACAAA  YGCSTATGCM                       90
```

( 2 ) INFORMATION FOR SEQ ID NO:16:

( i ) SEQUENCE CHARACTERISTICS:
        ( A ) LENGTH: 78 bases
        ( B ) TYPE: nucleic acid
        ( C ) STRANDEDNESS: double
        ( D ) TOPOLOGY: linear ( x i ) SEQUENCE DESCRIPTION: SEQ ID NO:16:

```
TCTAGAATTA  TGAAAAAGAA  TATCGCATTT  CTTCTTGCAT  CTATGTTCGT           50
TTTTCTATT   GCTACAAACG  CGTATGCM                                     78
```

( 2 ) INFORMATION FOR SEQ ID NO:17:

( i ) SEQUENCE CHARACTERISTICS:

(A) LENGTH: 78 bases
(B) TYPE: nucleic acid
(C) STRANDEDNESS: double
(D) TOPOLOGY: linear ( x i ) SEQUENCE DESCRIPTION: SEQ ID NO:17:

TCTAGAATTA TGAAGAAGAA TATTGCGTTC CTACTTGCCT CTATGTTTGT        50

CTTTTCTATA GCTACAAACG CGTATGCM        78

( 2 ) INFORMATION FOR SEQ ID NO:18:

( i ) SEQUENCE CHARACTERISTICS:
      (A) LENGTH: 78 bases
      (B) TYPE: nucleic acid
      (C) STRANDEDNESS: double
      (D) TOPOLOGY: linear ( x i ) SEQUENCE DESCRIPTION: SEQ ID NO:18:

TCTAGAATTA TGAAGAAGAA TATCGCATTT CTTCTTGCAT CTATGTTCGT        50

TTTTCTATT GCTACAAACG CGTATGCM        78

( 2 ) INFORMATION FOR SEQ ID NO:19:

( i ) SEQUENCE CHARACTERISTICS:
      (A) LENGTH: 78 bases
      (B) TYPE: nucleic acid
      (C) STRANDEDNESS: double
      (D) TOPOLOGY: linear ( x i ) SEQUENCE DESCRIPTION: SEQ ID NO:19:

TCTAGAATTA TGAAAAAAAA CATCGCATTT CTTCTTGCAT CTATGTTCGT        50

TTTTCTATT GCTACAAACG CGTATGCM        78

( 2 ) INFORMATION FOR SEQ ID NO:20:

( i ) SEQUENCE CHARACTERISTICS:
      (A) LENGTH: 78 bases
      (B) TYPE: nucleic acid
      (C) STRANDEDNESS: double
      (D) TOPOLOGY: linear ( x i ) SEQUENCE DESCRIPTION: SEQ ID NO:20:

TCTAGAATTA TGAAAAAAAA CATTGCCTTT CTTCTTGCAT CTATGTTCGT        50

TTTTCTATT GCTACAAACG CGTATGCM        78

( 2 ) INFORMATION FOR SEQ ID NO:21:

( i ) SEQUENCE CHARACTERISTICS:
      (A) LENGTH: 78 bases
      (B) TYPE: nucleic acid
      (C) STRANDEDNESS: double
      (D) TOPOLOGY: linear ( x i ) SEQUENCE DESCRIPTION: SEQ ID NO:21:

TCTAGAATTA TGAAGAAAAA CATCGCTTTT CTTCTTGCAT CTATGTTCGT        50

TTTTCTATT GCTACAAACG CGTATGCM        78

( 2 ) INFORMATION FOR SEQ ID NO:22:

( i ) SEQUENCE CHARACTERISTICS:
      (A) LENGTH: 78 bases
      (B) TYPE: nucleic acid
      (C) STRANDEDNESS: double
      (D) TOPOLOGY: linear ( x i ) SEQUENCE DESCRIPTION: SEQ ID NO:22:

TCTAGAATTA TGAAAAAGAA CATAGCGTTT CTTCTTGCAT CTATGTTCGT    50

TTTTCTATT GCTACAAACG CGTATGCM    78

( 2 ) INFORMATION FOR SEQ ID NO:23:

( i ) SEQUENCE CHARACTERISTICS:
      ( A ) LENGTH: 90 bases
      ( B ) TYPE: nucleic acid
      ( C ) STRANDEDNESS: double
      ( D ) TOPOLOGY: linear ( x i ) SEQUENCE DESCRIPTION: SEQ ID NO:23:

TCTAGAGGTT GAGGTGATTT TATGAAAAAA AACATCGCAT TTCTTCTTGC    50

ATCTATGTTC GTTTTTTCTA TTGCTACAAA CGCGTATGCM    90

METHODS AND COMPOSITIONS FOR SECRETION OF HETEROLOGOUS POLYPEPTIDES

FIELD OF THE INVENTION

This invention relates to signal sequences for the secretion of heterologous polypeptides from bacteria.

DESCRIPTION OF BACKGROUND AND RELATED ART

Secretion of heterologous polypeptides into the periplasmic space of E. coli and other prokaryotes or into their culture media is subject to a variety of parameters. Typically, vectors for secretion of a polypeptide of interest are engineered to position DNA encoding a secretory signal sequence 5' to the DNA encoding the polypeptide of interest. Two major recurring problems plague the secretion of such polypeptides. First, the signal sequence is often incompletely processed or removed, and second, the amount of polypeptide secreted is often low or undetectable. Attempts to overcome these problems fall into three major areas: trying several different signal sequences, mutating the amino acid sequence of the signal sequence, and altering the secretory pathway within the host bacterium.

A number of signal sequences are available for the first approach in overcoming secretion problems. Watson (*Nucleic Acids Research* 12: 5145–5164 (1984)) discloses a compilation of signal sequences. U.S. Pat. No. 4,963,495 discloses the expression and secretion of mature eukaryotic protein in the periplasmic space of a host organism using a prokaryotic secretion signal sequence DNA linked at its 3' end to the 5' end of the DNA encoding the mature protein. In particular, the DNA encoding E. coli enterotoxin signals, especially STII, are preferred. Chang et al. (i Gene 55:189–196 (1987)) discloses the use of the STII signal sequence to secrete hGH in E. coli. Gray et al. (*Gene* 39:247–245 (1985)) disclose the use of the natural signal sequence of human growth hormone and the use of the E. coli alkaline phosphatase promoter and signal sequence for the secretion of human growth hormone in E. coli. Wong et al. (*Gene* 68:193–203 (1988)) disclose the secretion of insulin-like growth factor 1 (IGF-1) fused to LamB and OmpF secretion leader sequences in E. coli, and the enhancement of processing efficiency of these signal sequences in the presence of a prlA4 mutation. Fujimoto et al. (*J. Biotech.* 8:77–86 (1988)) disclose the use of four different E. coli enterotoxin signal sequences, STI, STII, LT-A, and LT-B for the secretion of human epidermal growth factor (hEGF) in E. coli. Denefle et al. (*Gene* 85: 499–510 (1989)) disclose the use of OmpA and PhoA signal peptides for the secretion of mature human interleukin 1β.

Mutagenesis of the signal sequence has, in general, not been especially helpful in overcoming secretion problems. For example, Morioka-Fujimoto et al. (*J. Biol. Chem.* 266:1728–1732 (1991)) disclose amino acid changes in the LTA signal sequence that increased the amount of human epidermal growth factor secreted in E. coli. Goldstein et al. (*J. Bact.* 172:1225–1231 (1990)) disclose amino acid substitution in the hydrophobic region of OmpA effected secretion of nuclease A but not TEM β-lactamase. Matteucci et al. (*Biotech.* 4:51–55 (1986)) disclose mutations in the signal sequence of human growth hormone that enhance secretion of hGH. Lehnhardt et al. (*J. Biol. Chem.* 262:1716–1719 (1987)) disclose the effect of deletion mutations in OmpA signal peptide on secretion of nuclease A and TEM β-lactamase.

Finally, attempts at improving heterologous secretion in E. coli by modulating host machinery has so far shown limited improvement in overcoming secretion problems. For example, van Dijl et al. (*Mol. Gen. Genet.* 227:40–48 (1991)) disclose the effects of overproduction of the E. coli signal peptidase I (SPase I) on the processing of precursors. Klein et al. (*Protein Engineering* 5:511–517 (1992)) disclose that mutagenesis of the LamB signal sequence had little effect on secretion of bovine somatotropin, and that secretion properties of bovine somatotropin appear to be determined by the mature protein rather than by changes in the signal sequence. Perez-Perez et al. (*Bio/Technology* 12:179–180 (1994)) disclose that providing an E. coli host with additional copies of prlA4 (secY allele) and secE genes, which encode the major components of the "translocator", i.e., the molecular apparatus that physically moves proteins across the membrane, increased the ratio of mature to precursor hIL-6 from 1.2 to 10.8. U.S. Pat. No. 5,232,840 discloses novel ribosome binding sites useful in enhancing protein production in bacteria through enhanced and/or more efficient translation U.S. Pat. No. 5,082,783 discloses improved secretion of heterologous proteins by hosts such as yeasts by using promoters of at most intermediate strength with heterologous DNA secretion signal sequences. European Patent Application No. 84308928.5, filed 19 Dec. 1984, discloses promoter-ribosome binding site expression elements of general utility for high level heterologous gene expression.

The instant invention discloses the unexpected result that altered translation initiation regions with reduced translational strength provided essentially complete processing and high levels of secretion of a polypeptide of interest as compared to wild type signal sequences, and that many mammalian polypeptides require a narrow range of translation levels to achieve maximum secretion. A set of vectors with variant translation initiation regions provides a range of translational strengths for optimizing secretion of a polypeptide of interest.

SUMMARY OF THE INVENTION

One aspect of the invention is a method of optimizing secretion of a heterologous polypeptide of interest in a cell comprising comparing the levels of expression of the polypeptide under control of a set of nucleic acid variants of a translation initiation region, wherein the set of variants represents a range of translational strengths, and determining the optimal translational strength for production of mature polypeptide, wherein the optimal translational strength is less than the translational strength of the wild-type translation initiation region.

In a further aspect of the invention the variants are signal sequence variants, especially variants of the STII signal sequence.

BRIEF DESCRIPTION OF THE DRAWINGS

FIG. 1 depicts the sequence of the PhoA promoter, Trp and STII Shine-Dalgarno regions and STII signal sequence.

3

Figure 5:
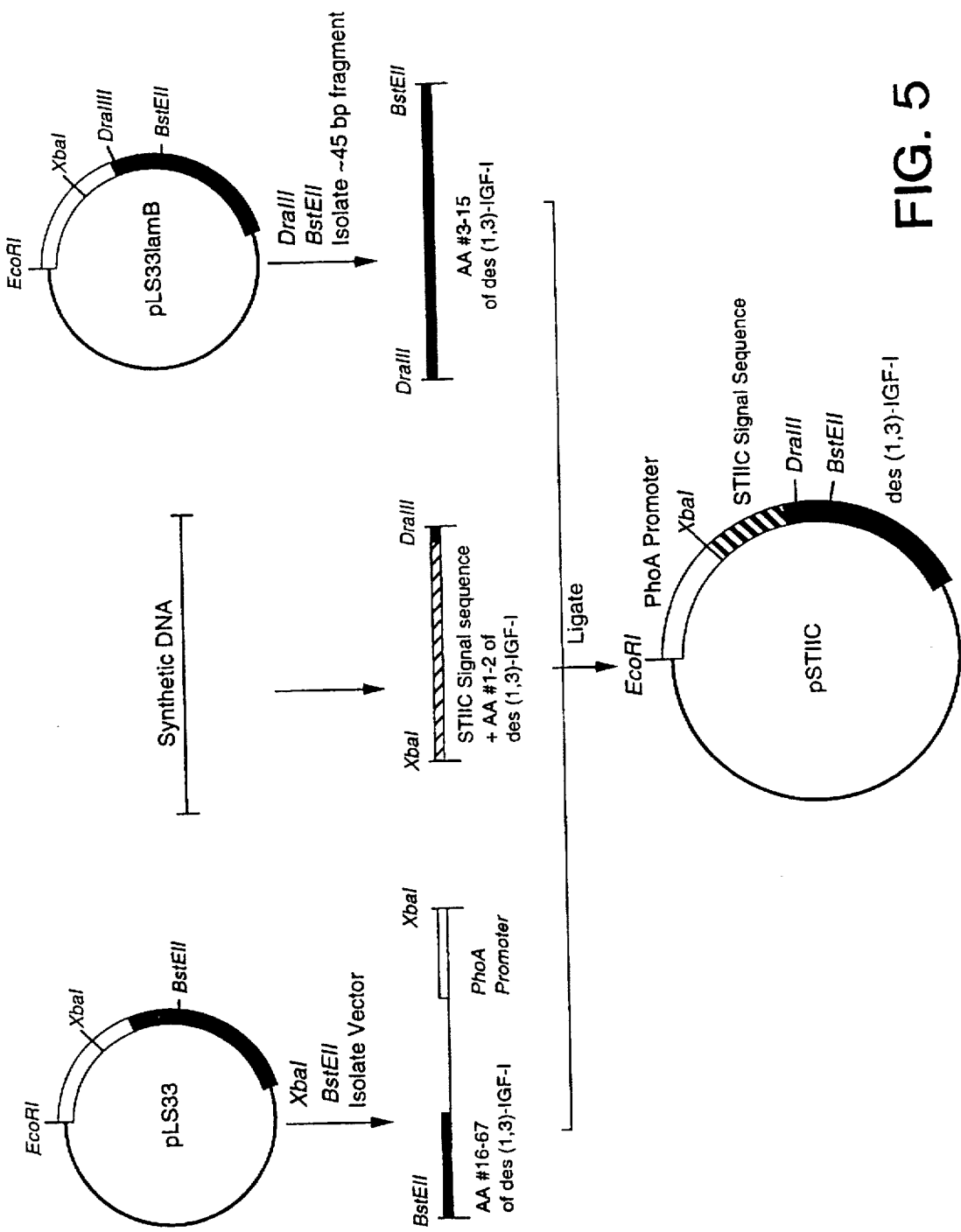

FIG. 5 is a diagram depicting construction of the plasmid pSTIIC.

Figure 6:
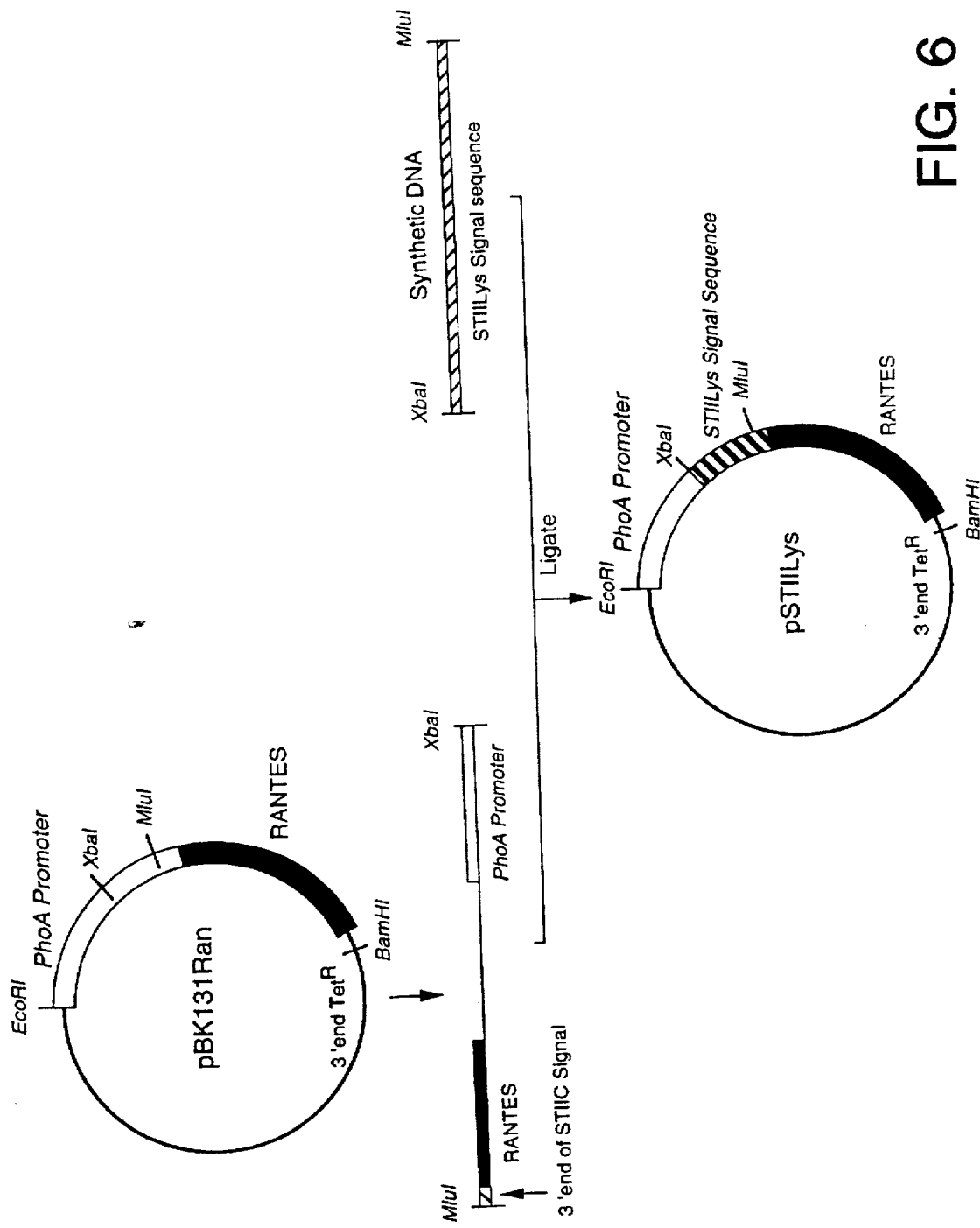

FIG. 6 is a diagram depicting construction of the plasmid pSTIILys.

Figure 7:
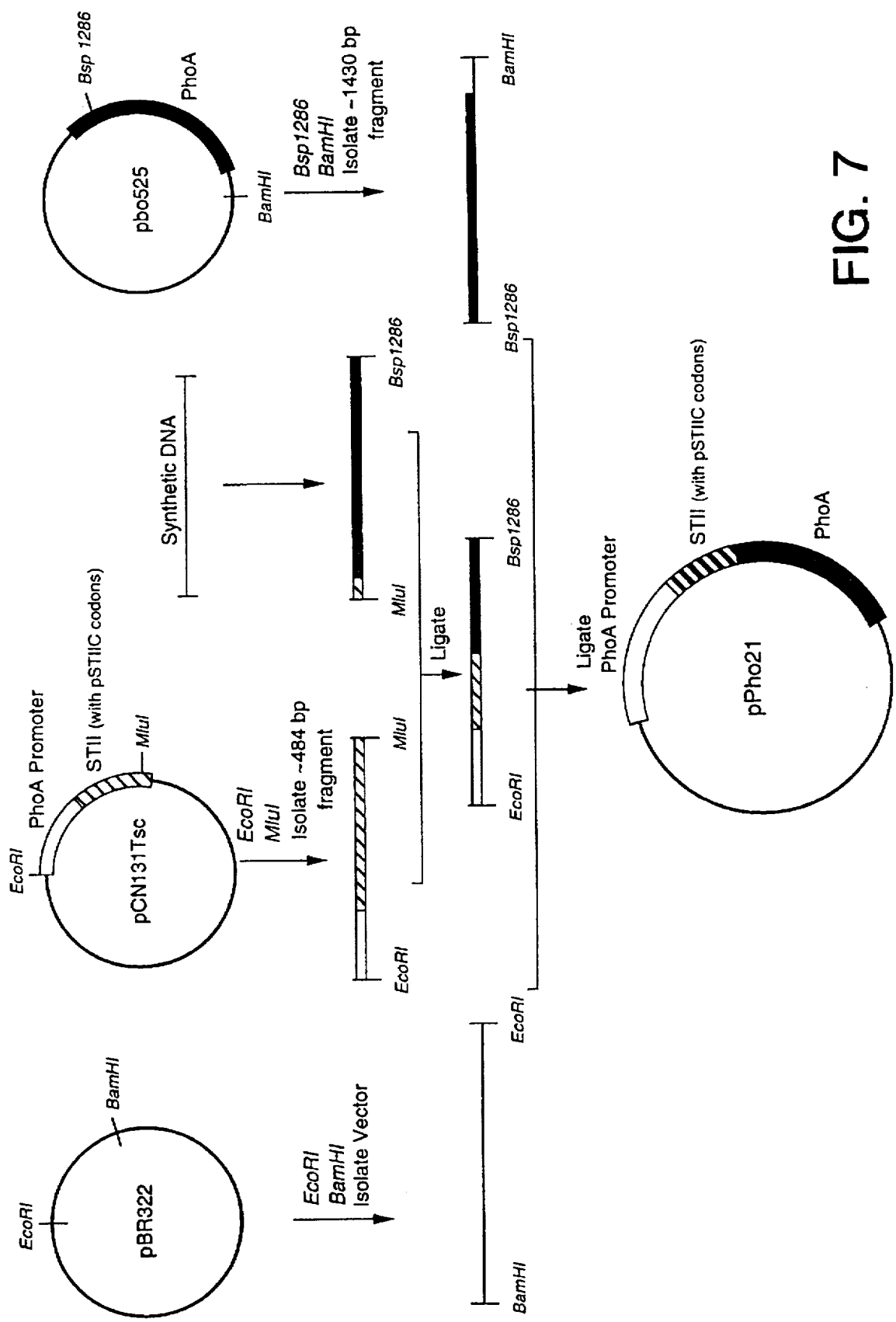

FIG. 7 is a diagram depicting construction of the plasmid pPho21.

Figure 8:
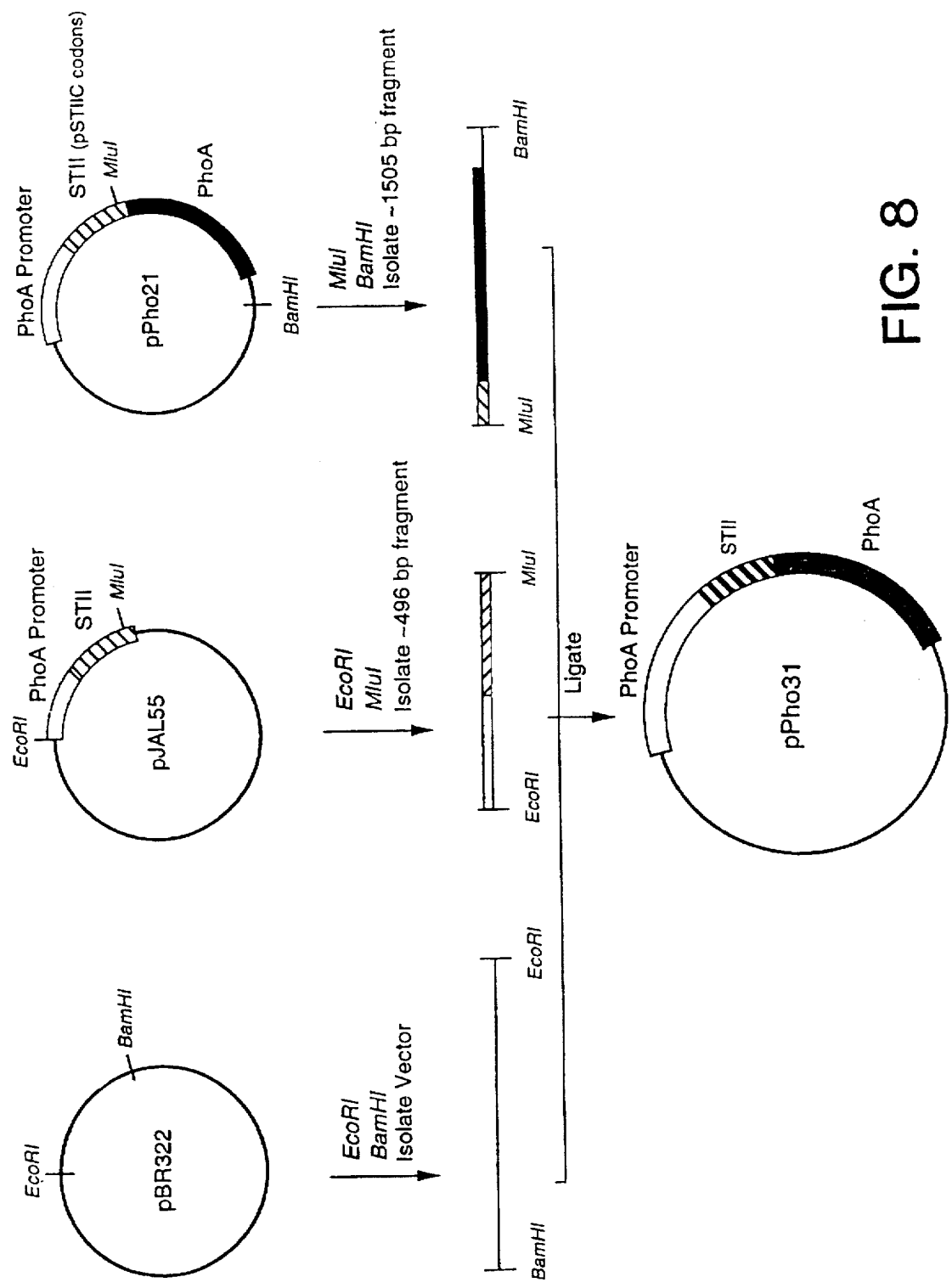

FIG. 8 is a diagram depicting construction of the plasmid pPho31.

Figure 9:
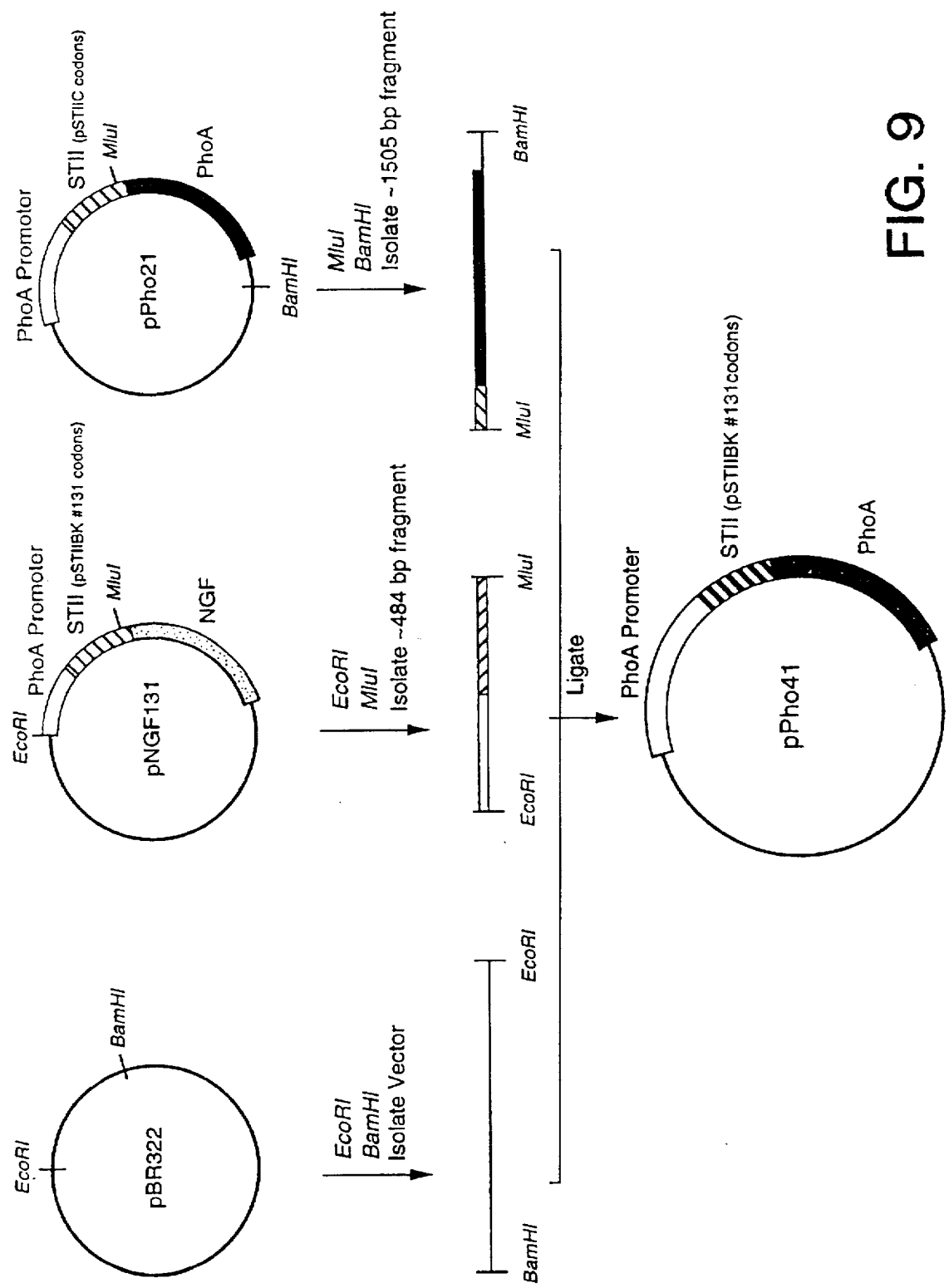

FIG. 9 is a diagram depicting construction of the plasmid pPho41.

Figure 10:
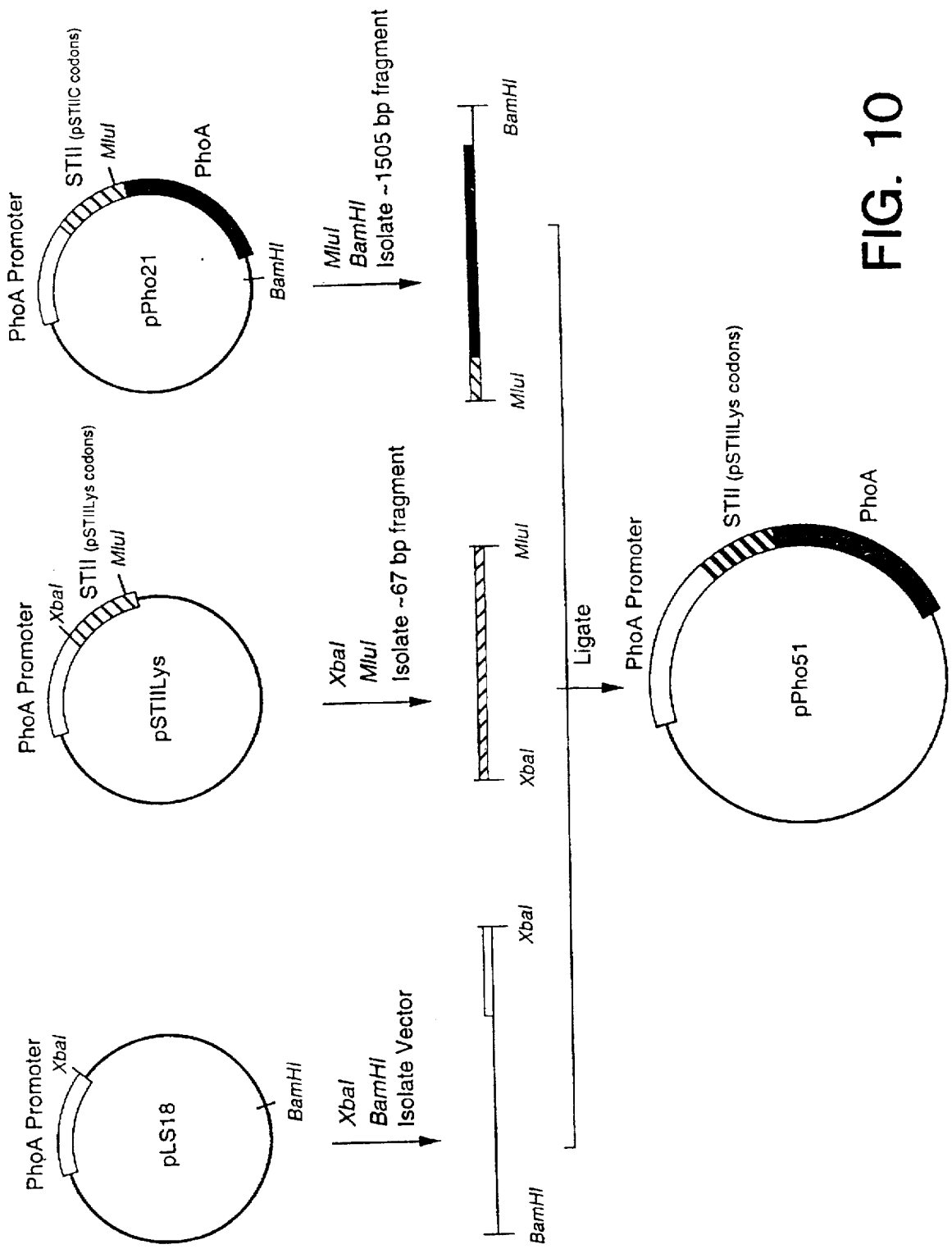

FIG. 10 is a diagram depicting construction of the plasmid pPho51.

Figure 11:
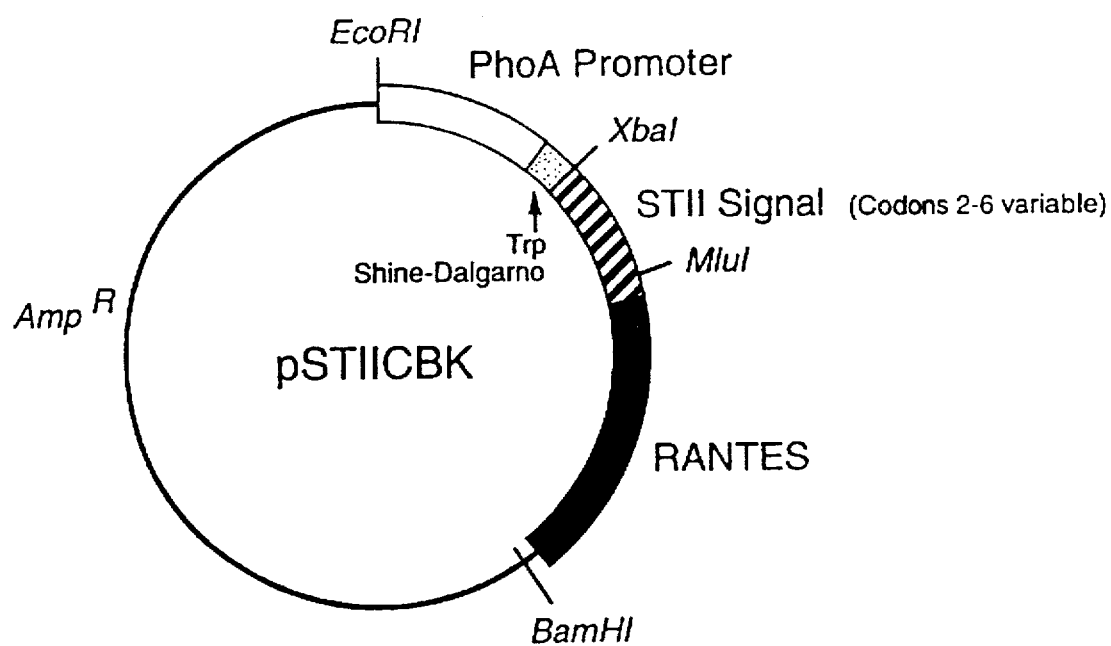

FIG. 11 is a diagram depicting relevant features of the library, pSTIICBK.

Figure 12:
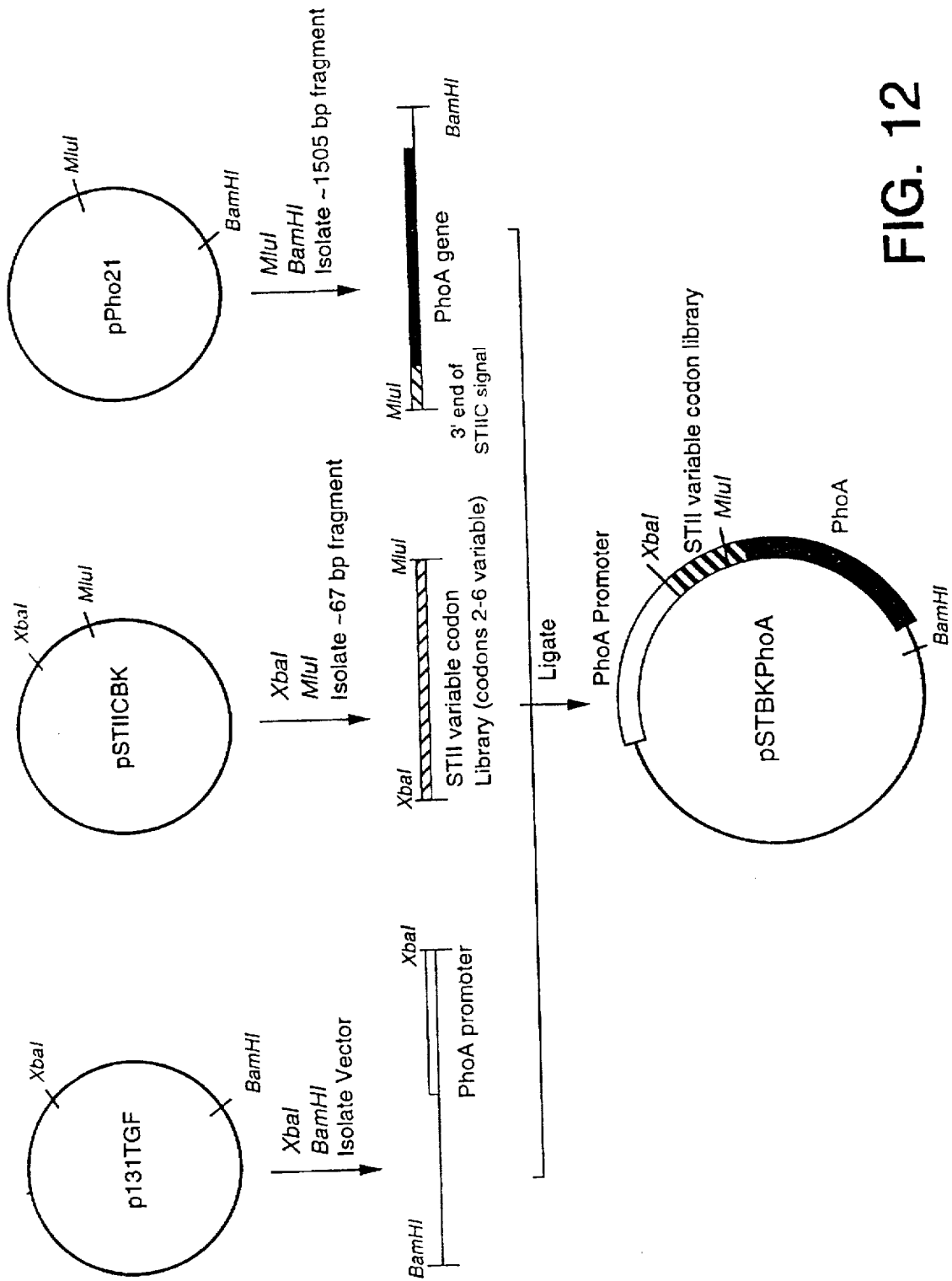

FIG. 12 is a diagram depicting construction of the library, pSTBKPhoA.

Figure 13:
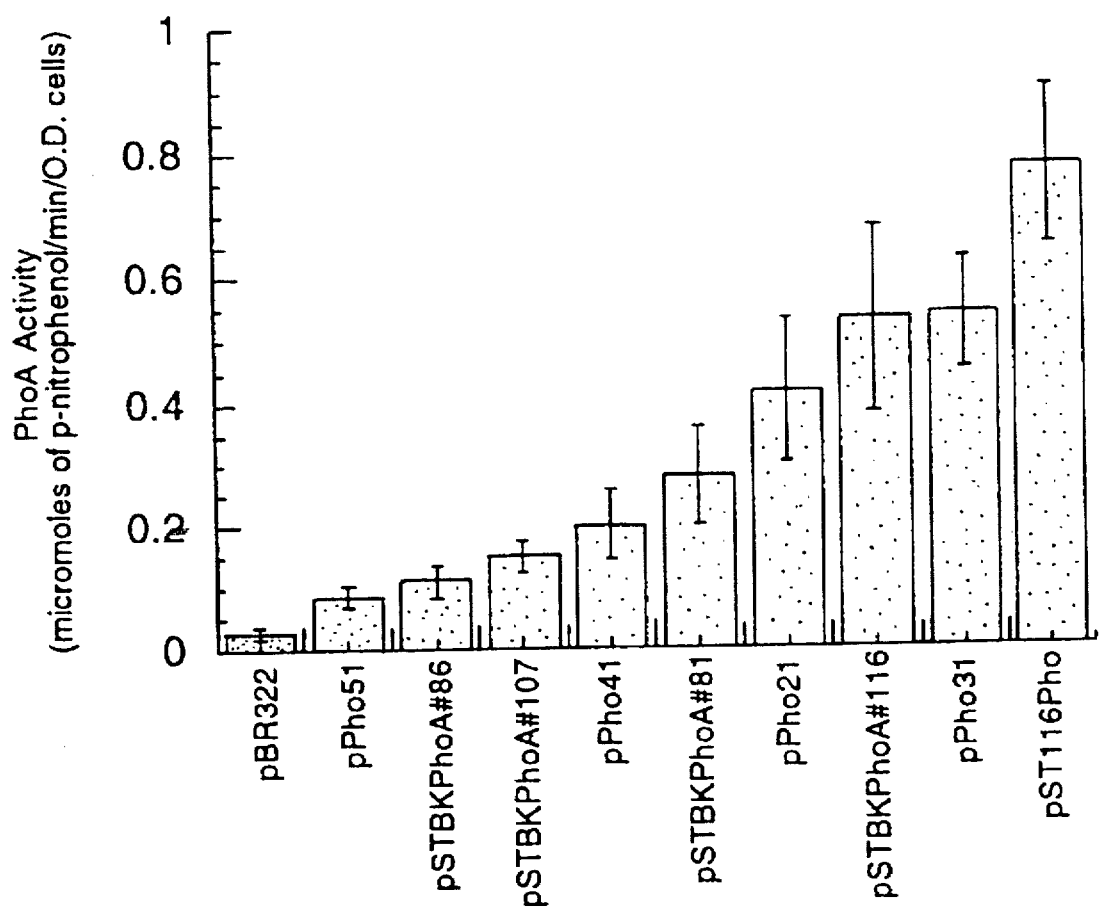

FIG. 13 is a graph depicting PhoA activity in isolates of the pSTBKPhoA library.

FIGS. 14A and 14B depict the nucleotide sequences of the listed STII signal sequence variants.

Figure 15:
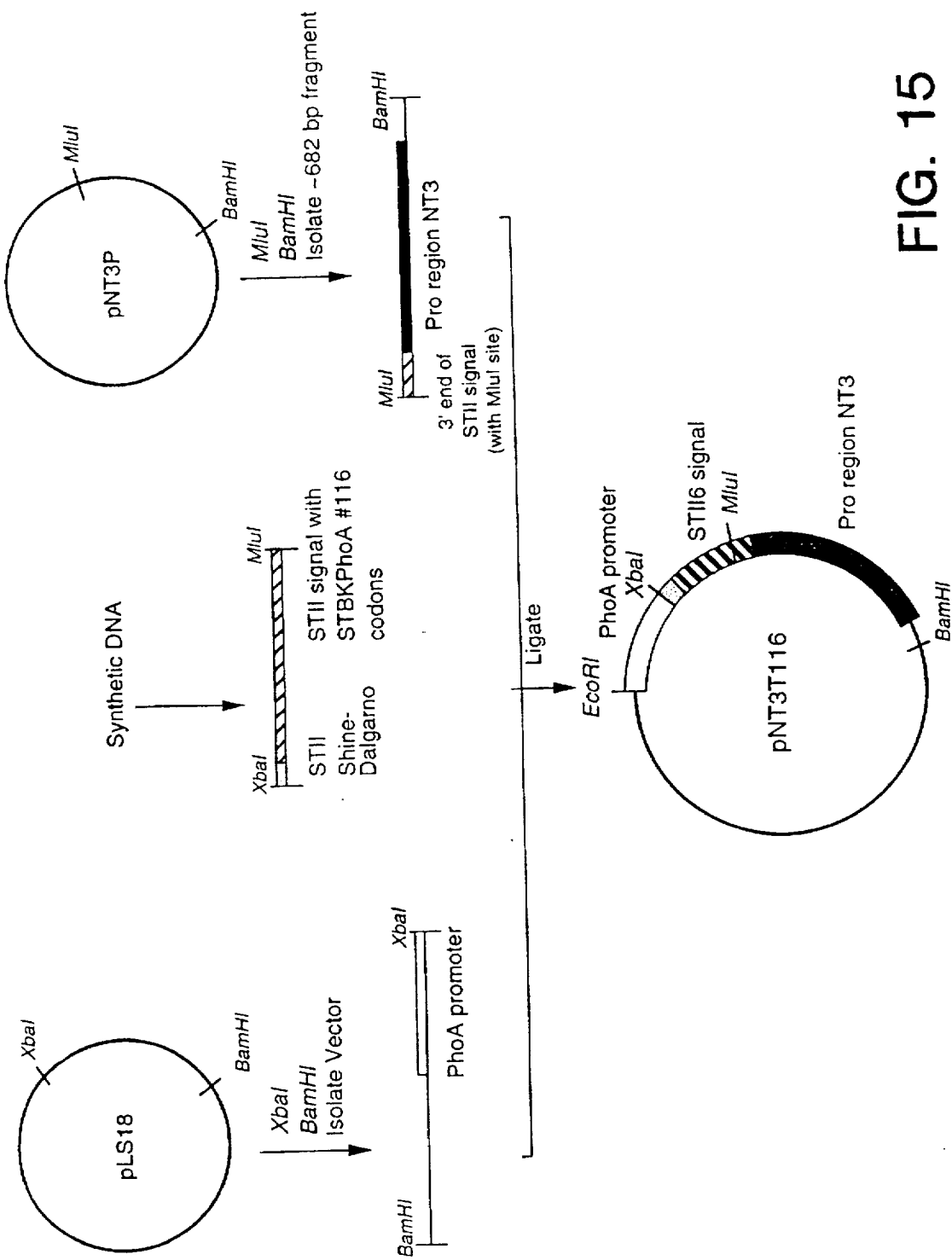

FIG. 15 is a diagram depicting construction of the plasmid pNT3PST116.

Figure 16:
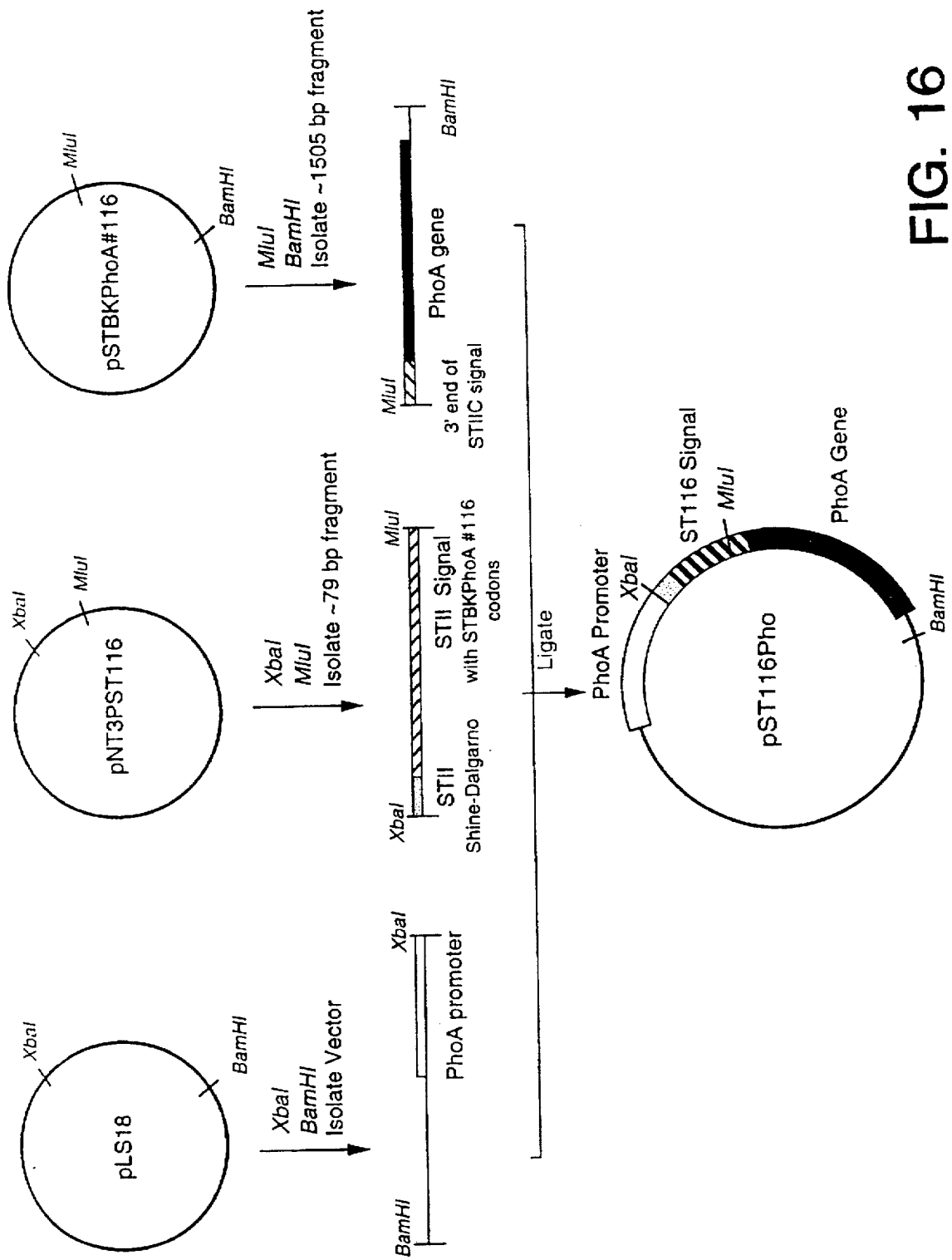

FIG. 16 is a diagram depicting construction of the plasmid pST116Pho.

Figure 17:
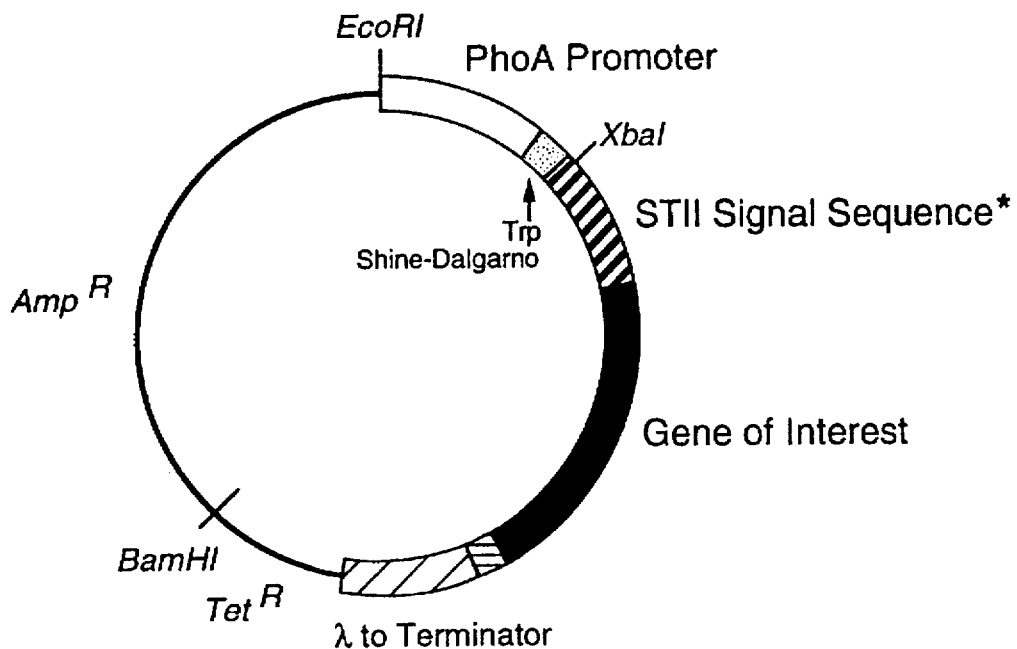

FIG. 17 is a diagram depicting relevant features of "category A" plasmids used in the examples.

Figure 18:
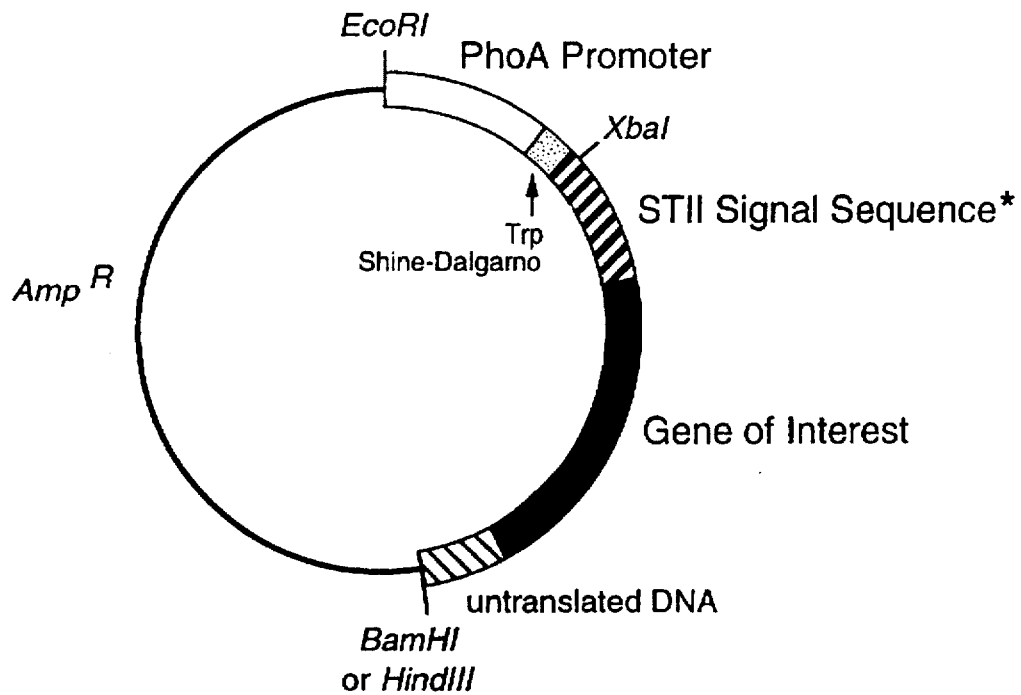

FIG. 18 is a diagram depicting relevant features of "category B" plasmids used in the examples.

Figure 19:
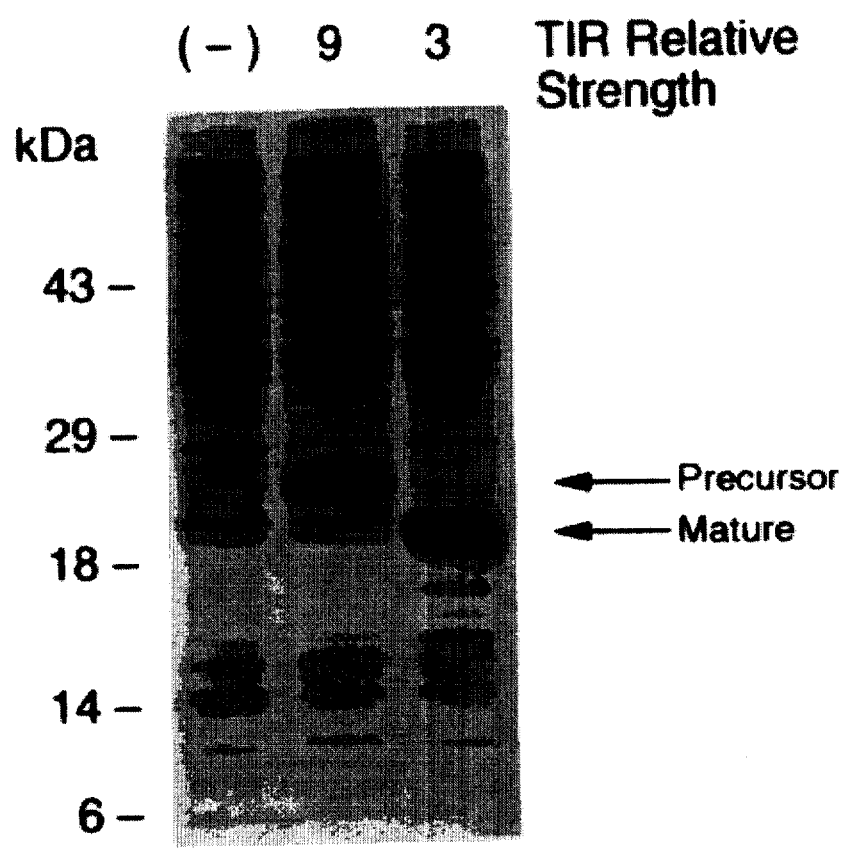

FIG. 19 is a photograph of a Coomassie blue stained polypeptide gel depicting secretion of mature ICAM-1 in *E. coli* under control of variant STII signal sequences. The TIR of relative strength 9 was provided by the pPho31 STII variant; the TIR of relative strength 3 was provided by the pPho41 STII variant. Precursor and mature forms of the polypeptide are indicated in the figure.

Figure 20:
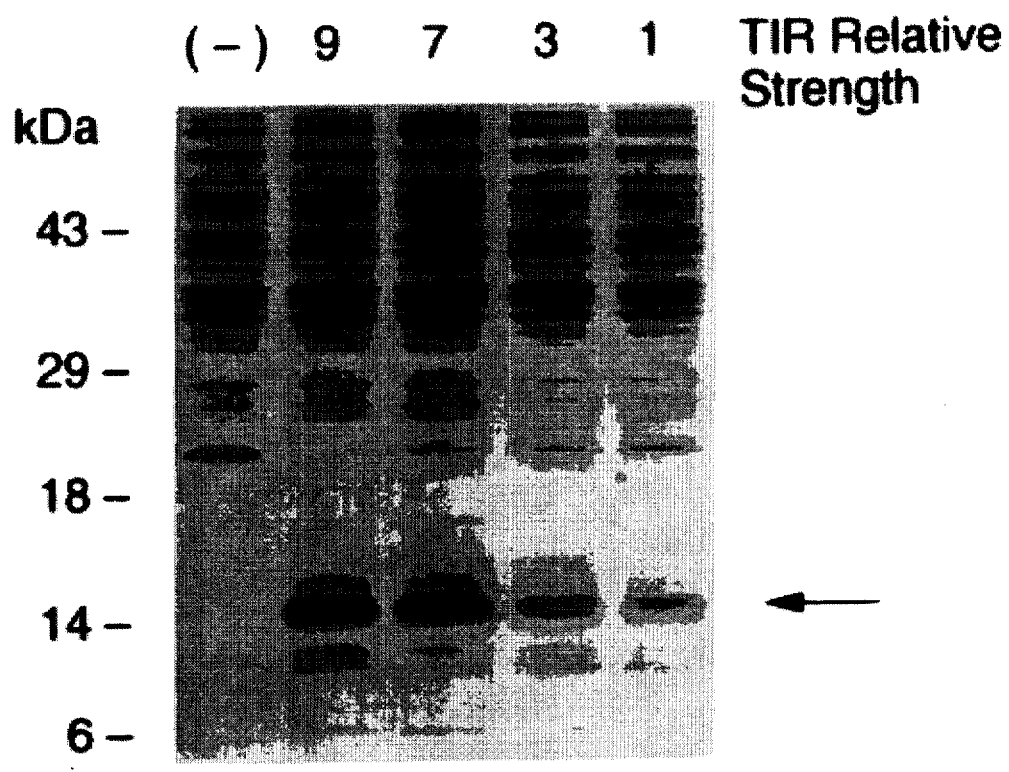

FIG. 20 is a photograph of a Coomassie blue stained polypeptide gel depicting secretion of mature NT3 in *E. coli* under control of variant STII signal sequences. The TIR of relative strength 9 was provided by the pPho31 STII variant; the TIR of relative strength 7 was provided by the pPho21 STII variant; the TIR of relative strength 3 was provided by the pPho41 STII variant; the TIR of relative strength 1 was provided by the pPho51 STII variant. The mature form of the polypeptide is indicated in the figure.

Figure 21:
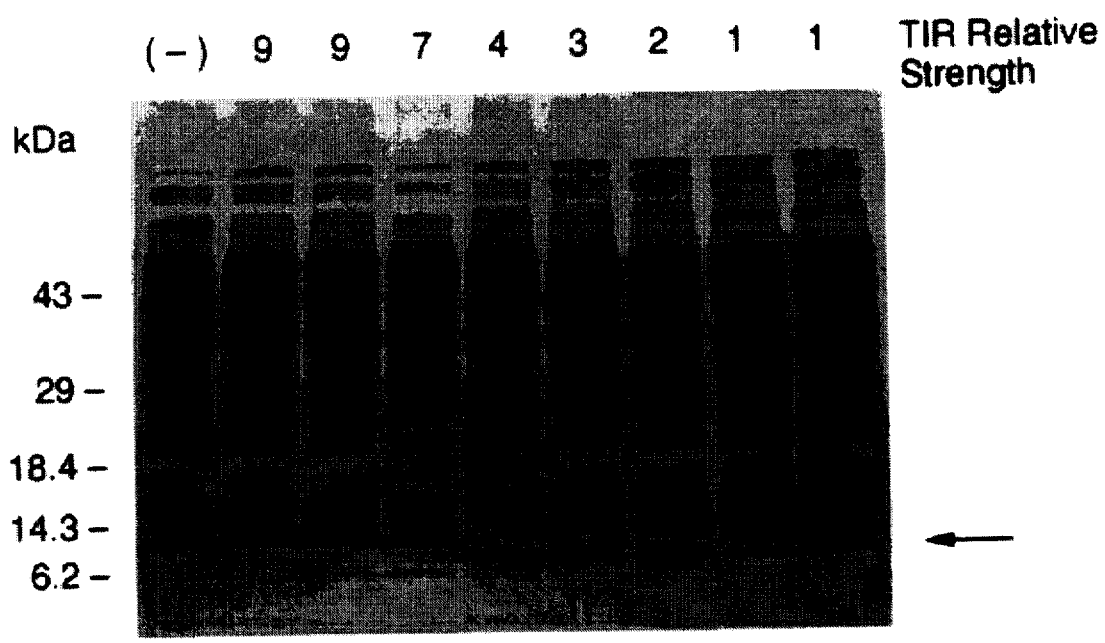

FIG. 21 is a photograph of a Coomassie blue stained polypeptide gel depicting secretion of mature RANTES in *E. coli* under control of variant STII signal sequences. Reading from left to right in the figure, the TIRs of relative strength 9 were provided by the pPho31 and the pSTBK-PhoA#116 STII variants; the TIR of relative strength 7 was provided by the pPho21 STII variant; the TIR of relative strength 4 was provided by the pSTBKPhoA#81 STII variant; the TIR of relative strength 3 was provided by the pPho41 STII variant; the TIR of relative strength 2 was provided by the pSTBKPhoA#107 STII variant; the TIRs of relative strength 1 were provided by the pSTBKPhoA#86 and the pPho51 STII variants. The mature form of the polypeptide is indicated in the figure.

DETAILED DESCRIPTION OF THE PREFERRED EMBODIMENTS

A. Definitions

The "translation initiation region" or TIR, as used herein refers to a region of RNA (or its coding DNA) determining the site and efficiency of initiation of translation of a gene of interest. (See, for example, McCarthy et al. *Trends in Genetics* 6:78–85 (1990).). A TIR for a particular gene can extend beyond the ribosome binding site (rbs) to include sequences 5' and 3' to the rbs. The rbs is defined to include, minimally, the Shine-Dalgarno region and the start codon, plus the bases in between, but can include the expanse of mRNA protected from ribonuclease digestion by bound ribosomes. Thus, a TIR can include an untranslated leader or the end of an upstream cistron, and thus a translational stop codon.

A "secretion signal sequence" or "signal sequence" as used herein refers to a sequence present at the amino terminus of a polypeptide that directs its translocation across a membrane. Typically, a precursor polypeptide is processed by cleavage of the signal sequence to generate mature polypeptide.

The term "translational strength" as used herein refers to a measurement of a secreted polypeptide in a control system wherein one or more variants of a TIR is used to direct secretion of a polypeptide encoded by a reporter gene and the results compared to the wild-type TIR or some other control under the same culture and assay conditions. For example, in these experiments translational strength is measured by using alkaline phosphatase as the reporter gene expressed under basal level control of the PhoA promoter, wherein secretion of the PhoA polypeptide is directed by variants of the STII signal sequence. The amount of mature alkaline phosphatase present in the host is a measure of the amount of polypeptide secreted, and can be quantitated relative to a negative control. Without being limited to any one theory, "translational strength" as used herein can thus include, for example, a measure of mRNA stability, efficiency of ribosome binding to the ribosome binding site, and mode of translocation across a membrane.

"Polypeptide" as used herein refers generally to peptides and polypeptides having at least about two amino acids.

B. General Methods

The instant invention demonstrates that translational strength is a critical factor in determining whether many heterologous polypeptides are secreted in significant quantities. Thus, for a given TIR, a series of amino acid or nucleic acid sequence variants can be created with a range of translational strengths, thereby providing a convenient means by which to adjust this factor for the optimal secretion of many different polypeptides. The use of a reporter gene expressed under the control of these variants, such as PhoA, provides a method to quantitate the relative translational strengths of different translation initiation regions. The variant or mutant TIRs can be provided in the background of a plasmid vector, thereby providing a set of plasmids into which a gene of interest may be inserted and its expression measured, so as to establish an optimum range of translational strengths for maximal expression of mature polypeptide.

Thus, for example, signal sequences from any prokaryotic or eukaryotic organism may be used. Preferably, the signal sequence is STII, OmpA, PhoE, LamB, MBP, or PhoA.

Mutagenesis of the TIR is done by conventional techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One preferred method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (*METHODS: A Companion to Methods in Enzymol.* 4:151–158 (1992)). Basically, a DNA fragment encoding the signal sequence and the beginning of the mature polypeptide is synthesized such that the third (and, possibly, the first and second, as described above) position of each of the first 6 to 12 codons is altered. The additional nucleotides downstream of these codons provide a site for the binding of a complementary primer used in making the bottom strand. Treatment of the top coding strand and the bottom strand primer with DNA polymerase I (Klenow) will result in a set of duplex DNA fragments containing randomized codons. The primers are designed to contain useful cloning sites that can then be used to insert the DNA fragments in an appropriate vector, thereby allowing amplification of the codon bank. Alternative methods include, for example, replacement of the entire rbs with random nucleotides (Wilson et al., *BioTechniques* 17:944–952 (1994)), and the use of phage display libraries (see, for example, Barbas et al., *Proc. Natl. Acad. Sci. U.S.A.* 89:4457–4461 (1992); Garrard et al., *Gene* 128:103–109 (1993)).

Typically, the TIR variants will be provided in a plasmid vector with appropriate elements for expression of a gene of interest. For example, a typical construct will contain a promoter 5' to the signal sequence, a restriction enzyme recognition site 3' to the signal sequence for insertion of a gene of interest or a reporter gene, and a selectable marker, such as a drug resistance marker, for selection and/or maintenance of bacteria transformed with the resulting plasmids.

Promoters suitable for use with prokaryotic hosts include the β-lactamase and lactose promoter systems (Chang et al., *Nature* 275:617–624 (1978); and Goeddel et al., *Nature* 281:544–548 (1979)), alkaline phosphatase, a tryptophan (Trp) promoter system (Goeddel, *Nucleic Acids Res.* 8(18) :4057–4074 (1980) and EP 36,776) and hybrid promoters such as the tac promoter (deBoer et al., *Proc. Natl. Acad. Sci. U.S.A.* 80:21–25 (1983).

Suitable promoting sequences for use with yeast hosts include the promoters for 3-phosphoglycerate kinase (Hitzeman et al., *J. Biol. Chem.* 255(24):12073–80 (1980)) or other glycolytic enzymes (Hess et al., *J. Adv. Enzyme Reg.* 7:149–67 (1968)); and Holland, *Biochemistry* 17:4900–4907 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Any reporter gene may be used which can be quantified in some manner. Thus, for example, alkaline phosphatase production can be quantitated as a measure of the secreted level of the phoA gene product. Other examples include, for example, the β-lactamase genes.

Preferably, a set of vectors is generated with a range of translational strengths into which DNA encoding a polypeptide of interest may be inserted. This limited set provides a comparison of secreted levels of polypeptides. The secreted level of polypeptides can be determined, for example, by a functional assays for the polypeptide of interest, if available, radioimmunoassays (RIA), enzyme-linked immunoassays (ELISA), or by PAGE and visualization of the correct molecular weight of the polypeptide of interest. Vectors so constructed can be used to transform an appropriate host. Preferably, the host is a prokaryotic host. More preferably, the host is *E. coli*.

Further details of the invention can be found in the following examples, which further define the scope of the invention. All references cited herein are expressly incorporated by reference in their entirety.

EXAMPLES

I. PLASMID CONSTRUCTS

A. Basid Plasmid Construction

All of the plasmids described in this patent application were constructed from a basic backbone of pBR322 (Sutcliffe, *Cold Spring Harb Symp Quant Biol* 43:77–90 (1978)). While the gene of interest expressed in each case varies, the transcriptional and translational sequences required for the expression of each gene were provided by the PhoA promoter and the Trp Shine-Dalgarno sequence (Chang et al., *Gene* 55:189–196 (1987)). Additionally, in the cases noted, a second Shine-Dalgarno sequence, the STII Shine-Dalgarno sequence (Picken et al., *Infect Immun* 42(1) :269–275 (1983)), was also be present. Secretion of the polypeptide was directed by the STII signal sequence or variants thereof (Picken et al., *Infect Inmun* 42(1):269–275 (1983)). The PhoA promoter, Trp and STII Shine-Dalgarno sequences and the sequence of the wild-type STII signal sequence are given in FIG. 1.

B. Construction of pLS33

Figure 2:
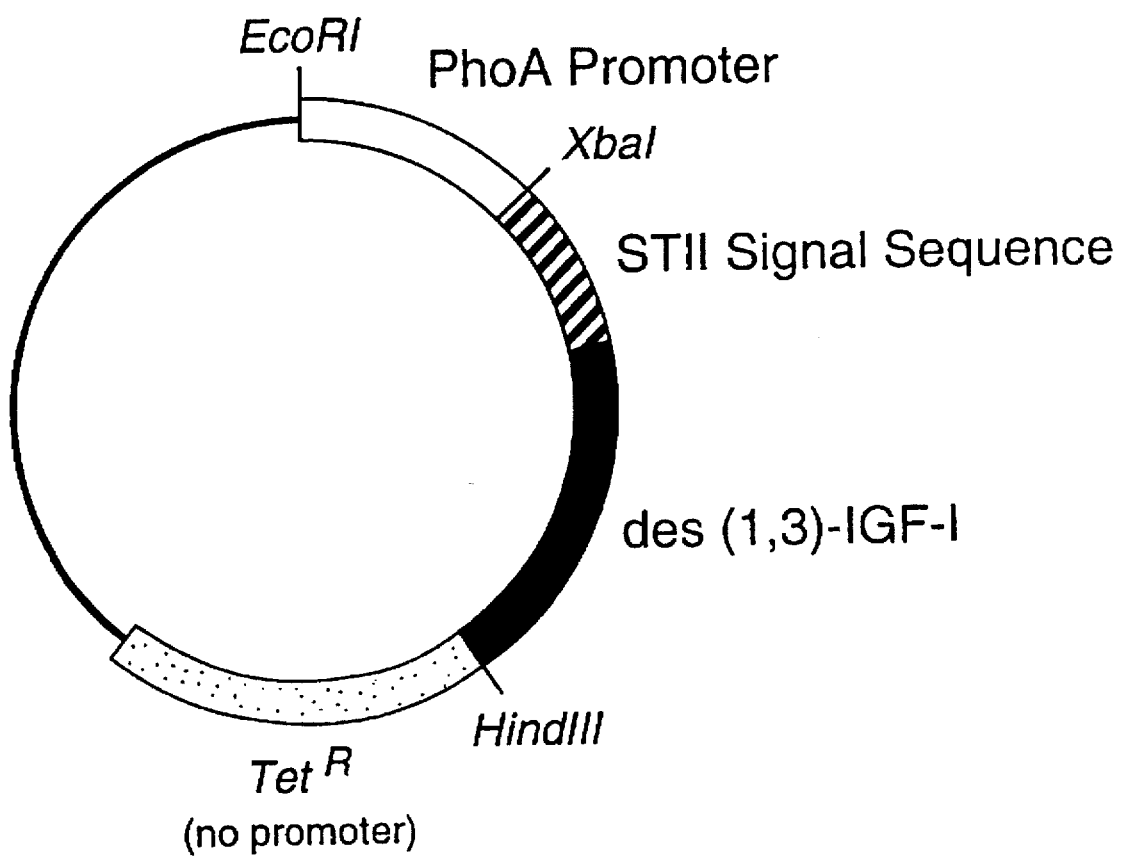
FIG. 2 is a diagram depicting relevant features of the plasmid pLS33.

The plasmid pLS33 was derived from phGH1 (Chang et al., *Gene* 55:189–196 (1987)), which was constructed for the expression of des(1,3)-IGF-L. In the plasmid pLS33, the gene encoding this version of insulin-like growth factor I (altered from the original sequence (Elmblad et al., *Third European Congress on Biotechnology III.* Weinheim: Verlag Chemie, pp. 287–292 (1984)) by the removal of the first three amino acids at the N-terminus) replaced the gene encoding human growth hormone. The construction pLS33 maintained the sequences for the PhoA promoter, Trp and STII Shine-Dalgarno regions and the wild-type STII signal sequence described for phGH1. However, the 3' end following the termination codon for des(1,3)-IGF-I was altered from that described for phGH1. In the case of pLS33, immediately downstream of the termination codon a HindIII restriction site was engineered, followed by the methionine start codon of the tetracycline resistance gene of pBR322 (Sutcliffe, *Cold Spring Harb Symp Quant Biol* 43:77–90 (1978)). A diagram of the plasmid pLS33 is given in FIG. 2.

C. Construction of pSTIIBK

A plasmid library containing a variable codon bank of the STII signal sequence (pSTIIBK) was constructed to screen for improved nucleotide sequences of this signal. The vector fragment for the construction of PSTIIBK was created by isolating the largest fragment when pLS33 was digested with XbaI and BstEII. This vector fragment contains the sequences that encode the PhoA promoter, Trp Shine-Dalgarno sequence and amino acids 16–67 of des(1,3)-IGF-I. The coding region for amino acids 3–15 of des(1,3)-IGF-I was provided by isolating the DraIII - BstEII fragment (approximately 45 bp) from another IGF-I expression plasmid, pLS33lamB. The variations in the nucleotide sequence for the STII signal were derived from the two strands of synthetic DNA listed below:

5'- GCATGTCTAGAATT ATG AAR AAR AAY ATH GCN TTY CTN CTN GCN TCN ATG TTY
GTN TTY TCN ATH GCT ACA AAC GCG TAT GCC ACTCT -3' (SEQ ID NO:1)

3'- CGA TGT TTG CGC ATA CGG TGAGACACGC-CACGACTT - 5' (SEQ ID NO:2)

R: A, G
Y: T, C
H: A, T, C
N: G, A, T, C

Figure 3:
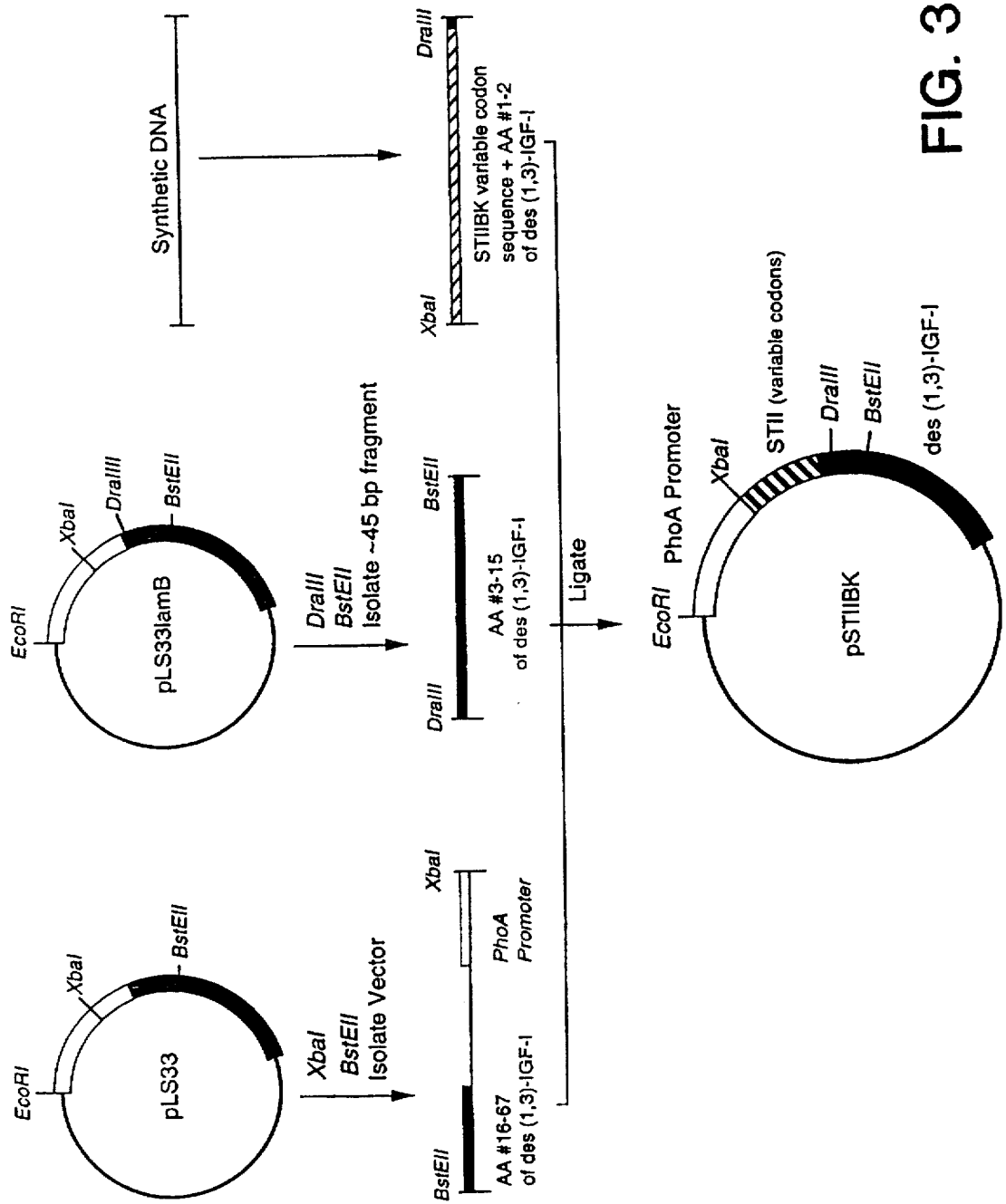
FIG. 3 is a diagram depicting construction of the library, PSTIIBK.

These two strands of synthetic DNA were annealed and treated with DNA Polymerase I (Klenow Fragment) to form duplex DNA of approximately 101 bp. This duplex DNA was then digested with XbaI and DraIII to generate the fragment of approximately 82 bp encoding the STII signal sequence with variable codons and the first two amino acids of des1,3)-IGF-I. These fragments were then ligated together as shown in FIG. 3 to construct the library, PSTI-IBK.

D. Selection of pSTIIBK#131

The plasmid library containing a variable codon bank of the STII signal sequence (PSTIIBK) was screened for improved growth of transformants and increased secretion of IGF-1. Basically, plasmids were transformed into host strain 27C7 (see below) and screened for enhanced ability to grow in a low phosphate medium (see Chang et al., supra) plus carbenicillin (50 µg/ml) based on OD600 measurements of cell density. Candidate colonies were tested for increased levels of IGF-1 secretion as follows. Colonies were inoculated into 3–5 ml LB plus carbenicillin (50 µg/ml) and grown at 37° C. with shaking for about 5–15 hours. Cultures were diluted 1:100 into 1–3 ml low phosphate medium plus Carbenicillin (50 µg/ml) and induced for 24 hours shaking at 37° C. The induced cultures were centrifuged in microcentrifuge tubes for 5 minutes. Supernatants were diluted into IGF RIA diluent and stored at −20° C. until assayed. The amount of IGF-1 secreted into the medium was measured by a radioimmunoassay.

Figure 4:
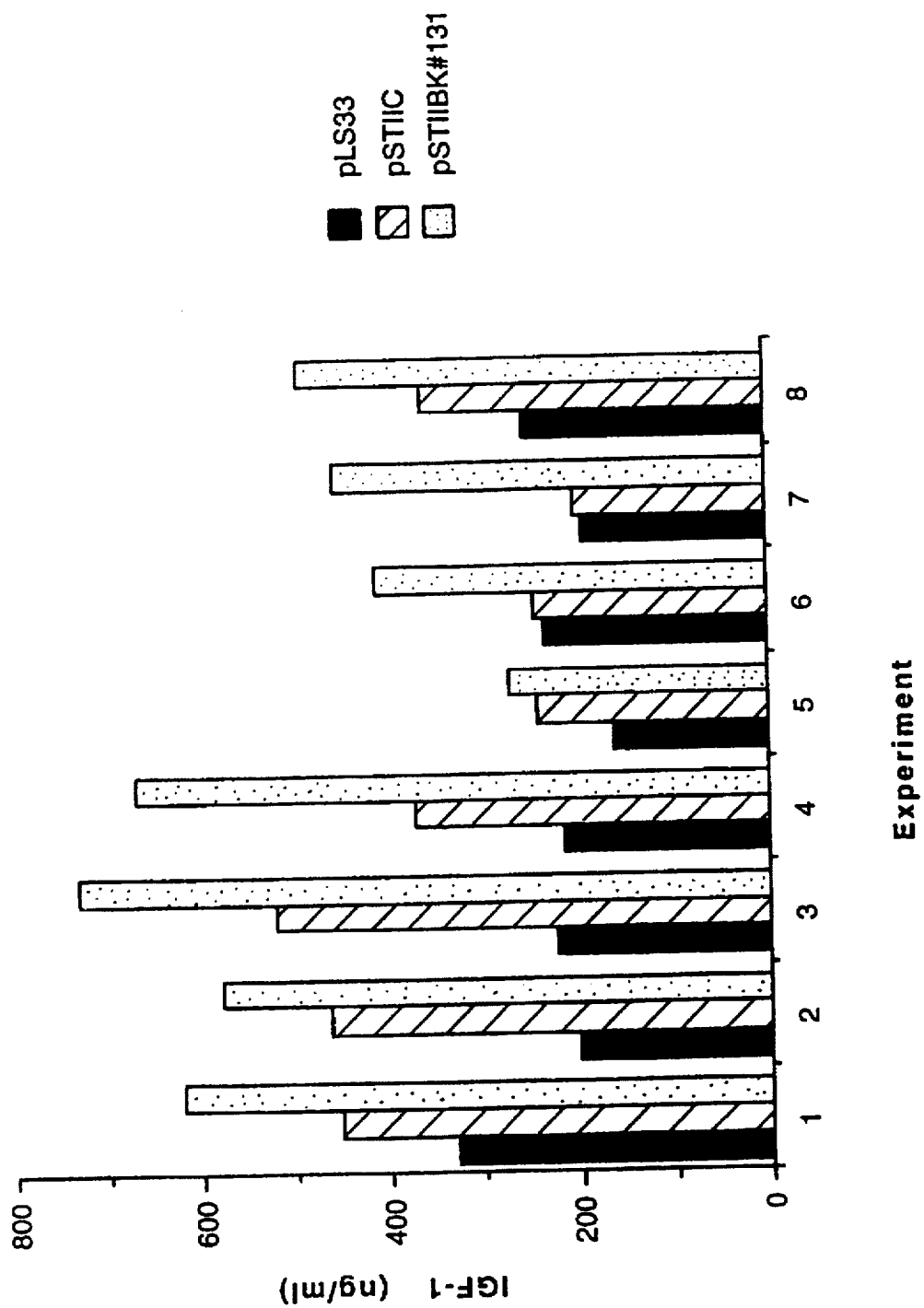
FIG. 4 is a graph depicting comparison of the level of expression of IGF-1, as measured by the amount of IGF-1 detected in culture supernatants, for pLS33, pSTIIBK#131, and pSTIIC. Experiments 1 to 8 represent measurements taken on 8 separate dates.

The level of expression of IGF-1, as measured by the amount of IGF-1 detected in culture supernatants, was compared for pLS33, pSTIIBK#131, and pSTIIC, in FIG. 4. The variant #131 consistently improved IGF-1 expression over the "original" or wild-type STII signal sequence. pSTIIC showed some slight improvement in expression over the wild-type sequence. pSTIIBK#131 differed from the wild-type STII in 12 codons and in the deletion of one Shine-Dalgarno sequence. pSTIIC was constructed as described below as a control plasmid having only one Shine-Dalgarno sequence and three codon changes near the extreme 3' end of the signal.

E. Construction of pSTIIC

In pSTIIC the STII Shine-Dalgarno sequence was removed from the plasmid pLS33. In addition, by incorporating silent mutations near the 3' end of the STII signal, an MluI site was engineered into pSTIIC. The identical fragments described for the construction of pSTIIBK (the vector from pLS33 and the approximately 45 bp DraIII-BstEII fragment from pLS331amB) were used for the construction of this plasmid. However, the synthetic DNA differed from that described above for the construction of pSTIIBK. For the construction of pSTIIC, the synthetic DNA coding for the STII signal sequence and the first two amino acids of des(1,3)-IGF-I was as follows:

5'-CTAGAATT ATG AAA AAG AAT ATC GCA TTT CTT CTT GCA TCT ATG TTC GTT
3'- TTAA TAC TTT TTC TTA TAG CGT AAA GAA GAA CGT AGA TAC AAG CAA

___MluI___
TTT TCT ATT GCT ACA AAC GCG TAT GCC ACTCT-3' (SEQ ID NO: 3)
AAA AGA TAA CGA TGT TTG CGC ATA CGG TG-5' (SEQ ID NO: 4)

These fragments were ligated together as illustrated in FIG. 5 to construct the plasmid pSTIIC.

F. Construction of pSTIILys

The plasmid pSTIILys contained an STII signal sequence that differs from the signal sequence of pSTIIC by only one nucleotide change at the position of the second codon. This signal sequence was constructed from synthetic DNA and placed in a pBR322-based vector for the expression of the polypeptide RANTES (Schall et al., J Immunol 141(3) :1018–1025 (1988)). The XbaI - MluI vector fragment for this construction was isolated from the plasmid pBK131Ran (a derivative of the plasmid pSTIIBK#131 with the gene encoding RANTES replacing the gene encoding des1,3)-IGF-I). This vector contained the PhoA promoter, Trp Shine-Dalgarno sequence, the last three amino acids of the STIIC signal sequence and the gene encoding the polypeptide RANTES. As illustrated in FIG. 6, this fragment was then ligated with the following strands of synthetic DNA to construct the plasmid pSTIILys (SEQ ID NO:3):

5'- CTAGAATT ATG AAG AAG AAT ATC GCA TTT CTT CTT GCA TCT ATG TTC GTT
3'- TTAA TAC TTC TTC TTA TAG CGT AAA GAA GAA CGT AGA TAC AAG CAA
TTT TCT ATT GCT ACA AA - 3' (SEQ ID NO:5)
AAA AGA TAA CGA TGT TTG CGC - 5' (SEQ ID NO:6)

G. Construction of Alkaline Phosphatase Plasmids

In order to determine a quantitative TIR value for each of the STII signal sequences described, the alkaline phosphatase gene of E. coli was used as a reporter gene. In each of these constructions, the PhoA gene was placed downstream of the PhoA promoter, Trp Shine-Dalgarno sequence and a version of the STII signal sequence. The plasmids pPho21, pPho31, pPho41 and pPho51 contained the signal sequences derived from pSTIIC, pLS33, pSTIIBK#131 and pSTIILys, respectively. In the case of pPho31, the construction also contained the STII Shine-Dalgarno region.

H. Construction of pPho21

The vector fragment for the construction of pPho21 was created by digesting pBR322 with EcoRI and BamHI and isolating the largest fragment. The PhoA promoter, Trp Shine-Dalgarno sequence and STIIC signal sequence (amino acids 1–20) were provided by isolating the approximately 484 bp fragment of pCN131Tsc following digestion with EcoRI and MluI. An identical fragment of approximately 484 bp could have also been generated from pSTIIC, a plasmid which has been described previously. The PhoA gene fragment (approximately 1430 bp) encoding amino acids 24–450 of alkaline phosphatase was generated from the plasmid pb0525 following digestion with Bsp1286 and BamHI (Inouye et al., *J Bacteriol* 146(2):668–675 (1981)). This Bsp1286 - BamHI fragment also contains approximately 142 bp of SV40 DNA (Fiers et al., *Nature* 273:113–120 (1978)) following the termination codon of alkaline phosphatase. Synthetic DNA was used to link the STII signal sequence with the PhoA gene. The sequence of this DNA encoding the last three amino acids of the STIIC signal sequence and amino acids 1–23 of alkaline phosphatase was as follows:

5'- CGCGTATGCCCGGACACCAGAAATGCCT-
GTTCTGGAAAACCGGGCTGCTCAGGGC-
GATATTACTG

3'- ATACGGGCCTGTGGTCTTTACGGACAA-
GACCTTTTGGCCCGACGAGTCCCGCTATAATGAC
CACCCGGCGGTGCT - 3' (SEQ ID NO:7)
GTGGGCCGCC - 5' (SEQ ID NO:8)

In order to facilitate the construction of this plasmid, the synthetic DNA was preligated to the EcoRI - MluI fragment of pCN131Tsc. This preligation generated a new fragment of about 575 bp. As illustrated in FIG. 7, the fragment generated from the preligation was then ligated together with the other fragments described to construct pPho21.

I. Construction of pPho31

The vector fragment for the construction of this plasmid was the identical vector described for pPho21. The PhoA promoter, Trp Shine-Dalgarno sequence, STII Shine-Dalgarno sequence and STII signal sequence (amino acids 1–20) were generated from pJAL55. The necessary fragment (approximately 496 bp) from pJAL55 was isolated following digestion with EcoRI and MluI. This EcoRI-MluI fragment only differed from the same region of pLS33 by an engineered MluI site starting at amino acid 20 of the STII signal sequence (as described for pSTIIC). The last three amino acids of the STIIC signal sequence and the sequence encoding the PhoA gene were provided by digesting the plasmid pPho21 with MluI and BamHI and isolating the approximately 1505 bp fragment. These fragments were ligated together as shown in FIG. 8 to yield pPho31.

J. Construction of pPho41

The vector fragment for the construction of this plasmid was the identical vector described for pPho21. The PhoA promoter, Trp Shine-Dalgarno sequence and STII signal sequence with pSTIIBK#131 codons (amino acids 1–20) were provided by isolating the approximately 484 bp EcoRI - MluI fragment of pNGF131. An identical fragment could have also been generated from pSTIIBK#131. The last three amino acids of the STIIC signal sequence and the sequence encoding the PhoA gene were provided by digesting the plasmid pPho21 with MluI and BamHI and isolating the approximately 1505 bp fragment. As illustrated in FIG. 9, these three fragments were then ligated together to construct pPho41.

K. Construction of pPho51

The vector fragment for the construction of pPho51 was generated by digesting the plasmid pLS18 with XbaI - BamHI and isolating the largest fragment. The plasmid pLS18 is a derivative of phGH1 (Chang et al., *Gene* 55:189–196 (1987)) and an identical vector would have been generated had phGH1 been used in place of pLS18. This XbaI BamHI vector contains the PhoA promoter and the Trp Shine-Dalgarno sequence. The STII signal sequence (amino acids 1–20) with pSTIILys codons was provided by isolating the approximately 67 bp fragment generated when pSTIILys was digested with XbaI and MluI. The last three amino acids of the STIIC signal sequence and the sequence encoding the PhoA gene were provided by digesting the plasmid pPho21 with MluI and BamHI and isolating the approximately 1505 bp fragment. A diagram for the construction of pPho51 is given in FIG. 10.

L. Construction of pSTIICBK

A second variable codon library of the STII signal sequence, pSTIICBK, was constructed. This second codon library was designed only to focus on the codons closest to the met initiation codon of the STII signal sequence. As illustrated in FIG. 11, pSTIICBK was a pBR322-based plasmid containing the gene encoding the polypeptide RANTES (Schall et al., *J Immunol* 141(3):1018–1025 (1988)) under the control of the PhoA promoter and the Trp Shine-Dalgarno sequence. In this plasmid, secretion of RANTES is directed by an STII signal sequence codon library derived from the following two strands of synthetic DNA:

5'- GCATGTCTAGAATT ATG AAR AAY ATH GCN TTT
CTT CTT GCA TCT ATG TTC
GTT TTT TCT ATT GCT ACA AAC GCG TAT GCC-3'
(SEQ ID NO:9)

3'- AGA TAA CGA TGT TTG CGC ATA CGG TGA - 5'
(SEQ ID NO:10)
R: A, G
Y: T, C
H: A, T, C
N: G, A, T, C

These two strands of synthetic DNA were annealed and treated with DNA Polymerase I (Klenow Fragment) to form duplex DNA of approximately 86 bp. This duplex DNA was then digested with XbaI and MluI to generate a fragment of approximately 67 bp encoding the first 20 amino acids of the STII signal sequence with variable codons at positions 2–6.

M. Construction of pSTBKPhoA

To increase the number of STII signal sequences available with differing relative TIR strengths, a convenient method of screening the codon library of pSTIICBK was required. The plasmid pSTBKPhoA was constructed as a solution to this problem. In the plasmid pSTBKPhoA, the STII codon library of pSTIICBK was inserted upstream of the PhoA gene and downstream of the PhoA promoter and the Trp Shine-Dalgarno sequence. PhoA activity thus provided a means by which to discriminate between different versions of the STII signal sequences.

The vector fragment for this construction was created by isolating the largest fragment when p131TGF was digested with XbaI and BamHI. An identical vector could have also been generated from phGH1 (Chang et al., *Gene* 55:189–196 (1987)). This vector contained the PhoA promoter and the Trp Shine-Dalgarno sequence. The codon library of the STII signal sequence was provided by isolating the approximately 67 bp fragment generated from pSTIICBK following digestion with XbaI and MluI. The last three amino acids of the STIIC signal sequence and the sequence encoding the PhoA gene were provided by digesting pPho21 with MluI and BamHI and isolating the approximately 1505 bp fragment. As illustrated in FIG. 12, the fragments were then ligated together to construct pSTBKPhoA.

N. Selection of pSTBKPhoA #81, 86, 107, 116

The plasmids pSTBKPhoA #81, 86, 107, 116 were selected from the codon library of pSTBKPhoA based on their basal level PhoA activity (FIG. 13). As listed in FIGS.

14A and 14B, each had a different nucleotide sequence encoding the STII signal sequence.

O. Construction of pST116Pho

This version of the STII signal sequence, ST116, combined the double Shine-Dalgarno sequence described by Chang et al. (*Gene* 55:189–196 (1987)) with the codons of the selected STII sequence pSTBKPhoA #116. This signal sequence was initially constructed in a plasmid designed for the secretion of the pro region of NT3 (pNT3PST116) and then was transferred into a plasmid containing the PhoA gene to obtain a relative TIR measurement (pST116Pho).

P. Construction of pNT3PST116

The vector for this construction was generated by digesting the plasmid pLS18 with XbaI and BamHI and isolating the largest fragment. The plasmid pLS18 was a derivative of phGH1 (Chang et al., *Gene* 55:189–196 (1987)) and an identical vector could have been generated from phGH1. This XbaI - BamHI vector contained the PhoA promoter and the Trp Shine-Dalgarno sequence. A fragment (approximately 682 bp) containing the last three amino acids of the STII signal sequence and the coding region for amino acids 19-138 of proNT3 (Jones et al., *Proc Natl Acad Sci* 87:8060–8064 (1990)) was generated from the plasmid pNT3P following digestion with MluI and BamHI. The plasmid pNT3P was a pBR322-based plasmid containing the PhoA promoter, STIIBK#131 version of the STII signal sequence and the coding region for amino acids 19-138 of proNT3. The strands of synthetic DNA listed below provided the sequence for the STII Shine-Dalgarno sequence and the first 20 amino acids of the STII signal sequence:

5'- CTAGAGGTTGAGGTGATTTT ATG AAA AAA AAC ATC GCA TTT CTT CTT GCA TCT

3'- TCCAACTCCACTAAAA TAC TTT TTT TTG TAG CGT AAA GAA GAA CGT AGA

ATG TTC GTT TTT TCT ATT GCT ACA AA - 3' (SEQ ID NO:11)

TAC AAG CAA AAA AGA TAA CGA TGT TTG CGC - 5' (SEQ ID NO:12)

These fragments were then ligated together as shown in FIG. 15 to construct pNT3PST116.

Q. Construction ST116Pho

The vector for the construction of this plasmid was the identical vector described for the construction of pNT3PST116. The STII Shine-Dalgarno sequence and the first 20 amino acids of the STII signal sequence (pSTBKPhoA#116 codons) were generated by isolating the approximately 79 bp fragment from pNT3PST116 following digestion with XbaI and MluI. The last three amino acids of the STIIC signal sequence and the sequence encoding the PhoA gene were isolated from pSTBKPhoA#116 following digestion with MluI and BamHI (approximately 1505 bp fragment). As illustrated in FIG. 16, ligation of these three fragments resulted in the construction of pST116Pho.

II. ALKALINE PHOSPHATASE ASSAY

In these experiments the altered TIR constructs utilizing the phoA reporter gene were assayed for relative translational strengths by a modification of the method of Amenura et al. (*J. Bacteriol.* 152:692–701, 1982). Basically, the method used was as follows. Plasmids carrying altered sequences, whether in the TIR, the Shine-Dalgarno region, the nucleotide sequence between the Shine Dalgarno region and the start codon of the signal sequence, or the signal sequence itself, whether amino acid sequence variants or nucleotide sequence variants, were used to transform *E. coli* strain 27C7 (ATCC 55,244) although any PhoA⁻ strain of *E. coli* could be used. Transformant colonies were inoculated into Luria-Bertani medium (LB) plus carbenicillin (50 μg/ml, Sigma, Inc.). Cultures were grown at 37° C. with shaking for 4–8 hr. The equivalent of 1 $OD_{600}$ of each culture was centrifuged, then resuspended in 1 ml strict AP media (0.4% glucose, 20 mM $NH_4Cl$, 1.6 mM $MgSO_4$, 50 mM KCl, 20 mM NaCl, 120 mM triethanolamine, pH 7.4) plus carbenicillin (50 μg/ml). The mixtures were then immediately placed at −20° C. overnight. After thawing, 1 drop toluene was added to 1 ml of thawed culture. After vortexing, the mixtures were transferred to 16×125 mm test tubes and aerated on a wheel at 37° C. for 1 hr. 40 μl of each toluene treated culture was then added to 1 ml 1M Tris-HCl pH 8 plus 1 mM PNPP (disodium 4-nitrophenyl phosphate hexahydrate) and left at room temperature for 1 hr. The reactions were stopped by adding 100 ml 1M sodium phosphate pH 6.5. The $OD_{410}$ was measured within 30 minutes. Enzyme activity was calculated as micromoles of p-nitrophenol liberated per minute per one $OD_{600}$ equivalent of cells.

The results are summarized in Table 1.

TABLE 1

Determination of TIR Relative Strength: Use of PhoA as a Reporter Gene

| TIR | PhoA Activity[1] | Standard Deviation | Relative Strength |
|---|---|---|---|
| pBR322 | 0.0279 | 0.0069 | — |
| pPho51[2] | 0.0858 | 0.0165 | 1 |
| pSTBKPhoA#86 | 0.1125 | 0.0246 | 1 |
| pSTBKPhoA#107 | 0.1510 | 0.0267 | 2 |
| pPho41[3] | 0.1986 | 0.0556 | 3 |
| pSTBKPhoA#81 | 0.2796 | 0.0813 | 4 |
| pPho21[4] | 0.4174 | 0.1145 | 7 |
| pSTBKPhoA#116 | 0.5314 | 0.1478 | 9 |
| pPho31[5] | 0.5396 | 0.0869 | 9 |
| pST116Pho | 0.7760 | 0.1272 | 13 |

[1]micromoles of p-nitrophenol/min/O. D. 600 cells
[2]same STII variant as pSTIILys
[3]same STII variant as pSTIIBK#131
[4]same STII variant as pSTIIC
[5]wild-type STII + MluI site, last codon GCC.

III. SECRETION OF HETEROLOGOUS POLYPEPTIDE EXAMPLES

The plasmids used in these examples were all very similar in design as described above. Rather than describe in detail each construction, the expression plasmids are described here in general terms. Although a different polypeptide of interest was expressed in each example, the only significant variation between these constructions was the nucleotide sequence following the 3' end of each coding region. Thus, for descriptive purposes, these plasmids were loosely grouped into the following two categories based on their 3' sequence:

Category A: Within about 25 bp 3' to the termination codon of each gene of interest began the sequence encoding the transcriptional terminator described by Scholtissek and Grosse (*Nucleic Acids Res.* 15(7):3185 (1987)) followed by the tetracycline resistance gene of pBR322 (Sutcliffe, *Cold Spring Harb Symp Quant Biol* 43:77–90 (1978)). Examples in this category included plasmids designed for the secretion of mature NGF (Ullrich et al., *Nature* 303:821–825 (1983)), mature TGF-β1 (Derynck et al., *Nature* 316:701–705 (1985)) and domains 1 and 2 of ICAM-1 (Staunton et al., *Cell* 52:925–933 (1988)). A schematic representation of these plasmids is given in FIG. 17.

Category B: Examples in this category included plasmids designed for the secretion of mature VEGF (Leung et al., Science 246:1306–1309 (1989)), mature NT3 (Jones et al., Proc. Natl. Acad. Sci. U.S.A. 87:8060–8064 (1990), RANTES (Schall et al., J Immunol 141(3):1018–1025 (1988), and PhoA. The termination codon in each of these plasmids is followed in the 3' direction by a segment of untranslated DNA (VEGF: approximately 43 bp; mature NT3: approximately 134 bp; RANTES: approximately 7 bp; PhoA: approximately 142 bp). Following this 3' untranslated region, the sequence of pBR322 was re-initiated beginning with either the HindIII site (as in the mature NT3 secretion plasmid) or the BamHI site (PhoA, VEGF, RANTES secretion plasmids). A schematic representation of the plasmids included in this category is illustrated in FIG. 18.

These plasmids were used to transform the host E. coli strain 27C7. Transformant colonies were inoculated into 3–5 ml LB+carbenicillin (50 μg/ml). The cultures were grown at 37° C. with shaking for 3–8 hours. The cultures were then diluted 1:100 into 3 ml low phosphate medium (Chang et al., supra) and grown for about 20 hours with shaking at 37° C. For each culture, an 0.5 $OD_{600}$ aliquot was centrifuged in a microfuge tube.

Each 0.5 $OD_{600}$ pellet was then prepared for gel analysis as follows. Each pellet was resuspended in 50 μl TE (10 mM Tris pH 7.6, 1 mM EDTA). After the addition of 10 μl 10% SDS, 5 μl reducing agent (1M dithiothreitol or 1M β-mercaptoethanol), the samples were heated at about 90° C. for 2 minutes and then vortexed. Samples were allowed to cool to room temperature, after which 500 μl acetone was added. The samples were vortexed and then left at room temperature for about 15 minutes. Samples were centrifuged for 5 minutes. The supernatants were discarded, and the pellets resuspended in 20 μl water, 5 μl reducing agent, 25 NOVEX 2X sample buffer. Samples were heated at about 90° C. for 3–5 minutes, then vortexed. After centrifugation for 5 minutes, supernatants were transferred to clean tubes and the pellets discarded. 5–10 μl of each sample was loaded onto 10 well, 1.0 mm NOVEX manufactured gel (San Diego, Calif.) and electrophoresed for 1.5–2 hr. at 120 volts. Gels were stained with Coomassie blue to visualize polypeptide (FIGS. 19–21).

To provide further quantitation of the results, some gels were analyzed by densitometry. These results are displayed in Table 2 below. Both the polypeptide gels and the densitometry results indicate that the heterologous polypeptides tested were consistently secreted more efficiently when an STII variant of reduced translation strength was used to direct secretion of that polypeptide.

TABLE 2

Examples of Improved Polypeptide Secretion By TIR Modification: Densitometer Scans of Polypeptide Gels

| Polypeptide | TIR (Relative Strength) | Amount Secreted (% total host polypeptide) |
|---|---|---|
| VEGF | 9 | 0.6 |
|  | 3 | 5.9 |
| NGF | 9 | 1.6 |
|  | 7 | 1.8 |
|  | 4 | 5.7 |
|  | 1 | 5.5 |
| RANTES | 9 | 0.3 |
|  | 9 | 0.2 |
|  | 7 | 0.4 |
|  | 4 | 3.9 |
|  | 3 | 3.6 |
|  | 2 | 3.5 |
|  | 1* | 1.6 |
|  | 1 | 1.7 |
| TGF-β1 | 7 | 1.7 |
|  | 3 | 9.2 |

*pSTBKPhoA#86 signal sequence

We claim:

1. A variant of the STII secretion signal sequence having the nucleic acid sequence comprising:

5'-TCTAGAGGTTGAGGTGATTTT ATG AAA AAG AAT ATC GCA TTT CTT CTT GCA TCT ATG TTC GTT TTT TCT ATT GCT ACA AAC GCS TAT GCM 3' (SEQ ID NO:15, wherein Y at position 81 is C).

2. A variant of the STII secretion signal sequence having the nucleic acid sequence comprising:

5'-TCTAGAGGTTGAGGTGATTTT ATG AAA AAG AAT ATC GCA TTT CTT CTT GCA TCT ATG TTC GTT TTT TCT ATT GCT ACA AAY GCG TAT GCM 3' (SEQ ID NO:15, wherein S at position 84 is G).

3. A variant of the STII secretion signal sequence having the nucleic acid sequence comprising:

5'-TCTAGAGGTTGAGGTGATTTT ATG AAA AAG AAT ATC GCA TTT CTT CTT GCA TCT ATG TTC GTT TTT TCT ATT GCT ACA AAY GCS TAT GCC 3' (SEQ ID NO:15, wherein M at position 90 is C).

4. A variant of the STII secretion signal sequence having the nucleic acid sequence comprising:

5'-TCTAGATT ATG AAA AAG AAT ATC GCA TTT CTT CTT GCA TCT ATG TTC GTT TTT TCT ATT GCT ACA AAC GCG TAT GCM 3' (SEQ ID NO:16).

5. A variant of the STII secretion signal sequence having the nucleic acid sequence comprising:

5'-TCTAGATT ATG AAG AAG AAT ATT GCG TTC CTA CTT GCC TCT ATG TTT GTC TTT TCT ATA GCT ACA AAC GCG TAT GCM 3' (SEQ ID. NO:17).

6. A variant of the STII secretion signal sequence having the nucleic acid sequence comprising:

5'-TCTAGATT ATG AAG AAG AAT ATC GCA TTT CTT CTT GCA TCT ATG TTC GTT TTT TCT ATT GCT ACA AAC GCG TAT GCM 3' (SEQ ID NO:18).

7. A variant of the STII secretion signal sequence having the nucleic acid sequence comprising:

5'-TCTAGATT ATG AAA AAA AAC ATC GCA TTT CTT CTT GCA TCT ATG TTC GTT TTT TCT ATT GCT ACA AAC GCG TAT GCM 3' (SEQ ID NO:19).

8. A variant of the STII secretion signal sequence having the nucleic acid sequence comprising:

5'-TCTAGATT ATG AAA AAA AAC ATT GCC TTT CTT CTT GCA TCT ATG TTC GTT TTT TCT ATT GCT ACA AAC GCG TAT GCM 3' (SEQ ID NO:20).

9. A variant of the STII secretion signal sequence having the nucleic acid sequence comprising:

5'-TCTAGATT ATG AAG AAA AAC ATC GCT TTT CTT CTT GCA TCT ATG TTC GTT TTT TCT ATT GCT ACA AAC GCG TAT GCM 3' (SEQ ID NO:21).

10. A variant of the STII secretion signal sequence having the nucleic acid sequence comprising:

5'-TCTAGATT ATG AAA AAG AAC ATA GCG TTT CTT CTT GCA TCT ATG TTC GTT TTT TCT ATT GCT ACA AAC GCG TAT GCM 3' (SEQ ID NO:22).

11. A variant of the STII secretion signal sequence having the nucleic acid sequence comprising:

5'-TCTAGAGGTTGAGGTGATTTT ATG AAA AAA AAC ATC GCA TTT CTT CTT GCA TCT ATG TTC GTT TTT TCT ATT GCT ACA AAC GCG TAT GCM 3' (SEQ ID NO:23).

* * * * *